(12) United States Patent
Jain et al.

(10) Patent No.: US 10,494,449 B2
(45) Date of Patent: Dec. 3, 2019

(54) FRACTIONATION OF CHARGED POLYSACCHARIDE

(71) Applicant: Lipoxen Technologies Limited, London (GB)

(72) Inventors: Sanjay Jain, London (GB); Ioannis Papaioannou, London (GB); Peter Laing, London (GB)

(73) Assignee: Lipoxen Technologies Limited, London (GB)

( * ) Notice: Subject to any disclaimer, the term of this patent is extended or adjusted under 35 U.S.C. 154(b) by 0 days.

(21) Appl. No.: 15/821,483

(22) Filed: Nov. 22, 2017

(65) Prior Publication Data

US 2018/0298114 A1 Oct. 18, 2018

Related U.S. Application Data

(63) Continuation of application No. 14/924,634, filed on Oct. 27, 2015, now Pat. No. 9,828,443, which is a
(Continued)

(30) Foreign Application Priority Data

Feb. 23, 2015 (EP) .................................. 05251016

(51) Int. Cl.
*C08B 37/00* (2006.01)
*A61K 47/61* (2017.01)
(Continued)

(52) U.S. Cl.
CPC .......... *C08B 37/0006* (2013.01); *A61K 47/61* (2017.08); *B01D 15/361* (2013.01);
(Continued)

(58) Field of Classification Search
CPC .... B01D 15/36; B01D 15/363; B01D 15/424; B01D 15/426; G01N 30/26; G01N 30/28; G01N 30/34; G01N 30/38; C08B 37/0006
See application file for complete search history.

(56) References Cited

U.S. PATENT DOCUMENTS 3,637,489 A * 1/1972 Haller .................. G01N 30/482
210/656
4,301,153 A * 11/1981 Rosenberg ........... A61K 31/715
424/529

(Continued)

OTHER PUBLICATIONS

Silver et al. The K1 Capsular Polysaccharide of *Escherichia coli*. Reviews of Infectious Diseases, vol. 10, Supplement 2. Microbial Surfaces: Determinants of Virulence and Host Responsiveness (Jul.-Aug. 1988), pp. 5282-5286. (Year: 1988).*

(Continued)

*Primary Examiner* — Katherine Zalasky
(74) *Attorney, Agent, or Firm* — Entralta P.C.; James F. Fleming; Peter D. Weinstein

(57) ABSTRACT

Polydisperse and charged polysaccharides are fractionated into low polydispersity fractions (preferably having pd<1.1), each containing species within a narrow range of molecular weights. An aqueous solution of the polydisperse polysaccharides is contacted with an ion exchange resin in a column and the polysaccharides are subjected to selective elution by aqueous elution buffer. The selective elution consists of at least 3 sequential elution buffers having different and constant ionic strength and/or pH and in which the subsequent buffers have ionic strength and/or pH than those of the preceding step. The new preparations are particularly suitable for the production of PSA-derivatised therapeutic agents intended for use in humans and animals.

5 Claims, 31 Drawing Sheets

Related U.S. Application Data continuation of application No. 14/155,754, filed on Jan. 15, 2014, now Pat. No. 9,200,052, which is a continuation of application No. 11/660,133, filed as application No. PCT/GB2005/003149 on Aug. 12, 2005, now Pat. No. 8,652,334, which is a continuation-in-part of application No. PCT/GB2004/003511, filed on Aug. 12, 2004.

(51) Int. Cl.

| | | |
|---|---|---|
| *B01D 15/36* | (2006.01) | |
| *C07K 14/61* | (2006.01) | |
| *C07K 1/18* | (2006.01) | |
| *B01D 15/42* | (2006.01) | |

(52) U.S. Cl.
CPC ......... *B01D 15/362* (2013.01); *B01D 15/363* (2013.01); *B01D 15/424* (2013.01); *C07K 1/18* (2013.01); *C07K 14/61* (2013.01); *C08B 37/0003* (2013.01); *B01D 15/426* (2013.01)

(56) References Cited

U.S. PATENT DOCUMENTS

| | | | | |
|---|---|---|---|---|
| 4,461,833 A * | 7/1984 | Gordon | ........... | C12N 9/6421 210/656 |
| 5,089,138 A * | 2/1992 | Shibata | ........... | B01D 15/08 210/198.2 |
| 5,208,160 A * | 5/1993 | Kikyotani | ........... | G01N 30/88 210/638 |
| 5,210,226 A * | 5/1993 | Pandey | ........... | C07D 313/00 210/656 |
| 5,252,216 A * | 10/1993 | Folena-Wasserman | ........... | B01D 15/1871 210/635 |
| 5,268,097 A * | 12/1993 | Girot | ........... | B01D 15/206 210/198.2 |
| 5,316,680 A * | 5/1994 | Frechet | ........... | G01N 30/88 210/198.2 |
| 5,475,120 A * | 12/1995 | Rao | ........... | C07C 69/00 210/656 |
| 5,846,951 A * | 12/1998 | Gregoriadis | ........... | A61K 9/1271 514/54 |
| 6,042,723 A * | 3/2000 | Duval | ........... | B01D 15/3833 210/198.2 |
| 6,221,250 B1 * | 4/2001 | Stafstrom | ........... | G01N 30/34 210/101 |
| 6,248,570 B1 * | 6/2001 | Michon | ........... | C08B 37/00 435/101 |
| 6,451,987 B1 * | 9/2002 | Staby | ........... | C07K 1/18 210/656 |
| 2003/0224346 A1 * | 12/2003 | Karlsson | ........... | B01J 41/20 435/4 |
| 2004/0077090 A1 * | 4/2004 | Short | ........... | C12N 15/102 506/1 |
| 2007/0144973 A1 * | 6/2007 | Tsonev | ........... | B01D 15/168 210/659 |
| 2008/0029455 A1 * | 2/2008 | Jones | ........... | B01D 15/327 210/638 |

OTHER PUBLICATIONS

Roberts et al. Molecular Cloning and Analysis of Genes for Production of K5, K7, K12, and K92 Capsular Polysaccharides in *Escherichia coli*. Journal of Bacteriology, Dec. 1986, p. 1228-1233. (Year: 1986).*

Adlam et al. Production of colominic acid by Pasteurella haemolytica serotype A2 organisms. FEMS Microbiology Letters 42 (1987) 23-25. (Year: 1987).*

Devi et al. Identity between Polysaccharide Antigens of Moraxella nonliquefaciens, Group B *Neisseria meningitidis*, and *Escherichia coli* Ki (Non-O Acetylated). Infection and Immunity, Feb. 1991, p. 732-736. (Year: 1991).*

McGuire et al. The Structure and Chemistry of Colominic Acid. Biochemistry. vol. 3, No. 2, Feb. 1964, p. 247-251. (Year: 1964).*

* cited by examiner

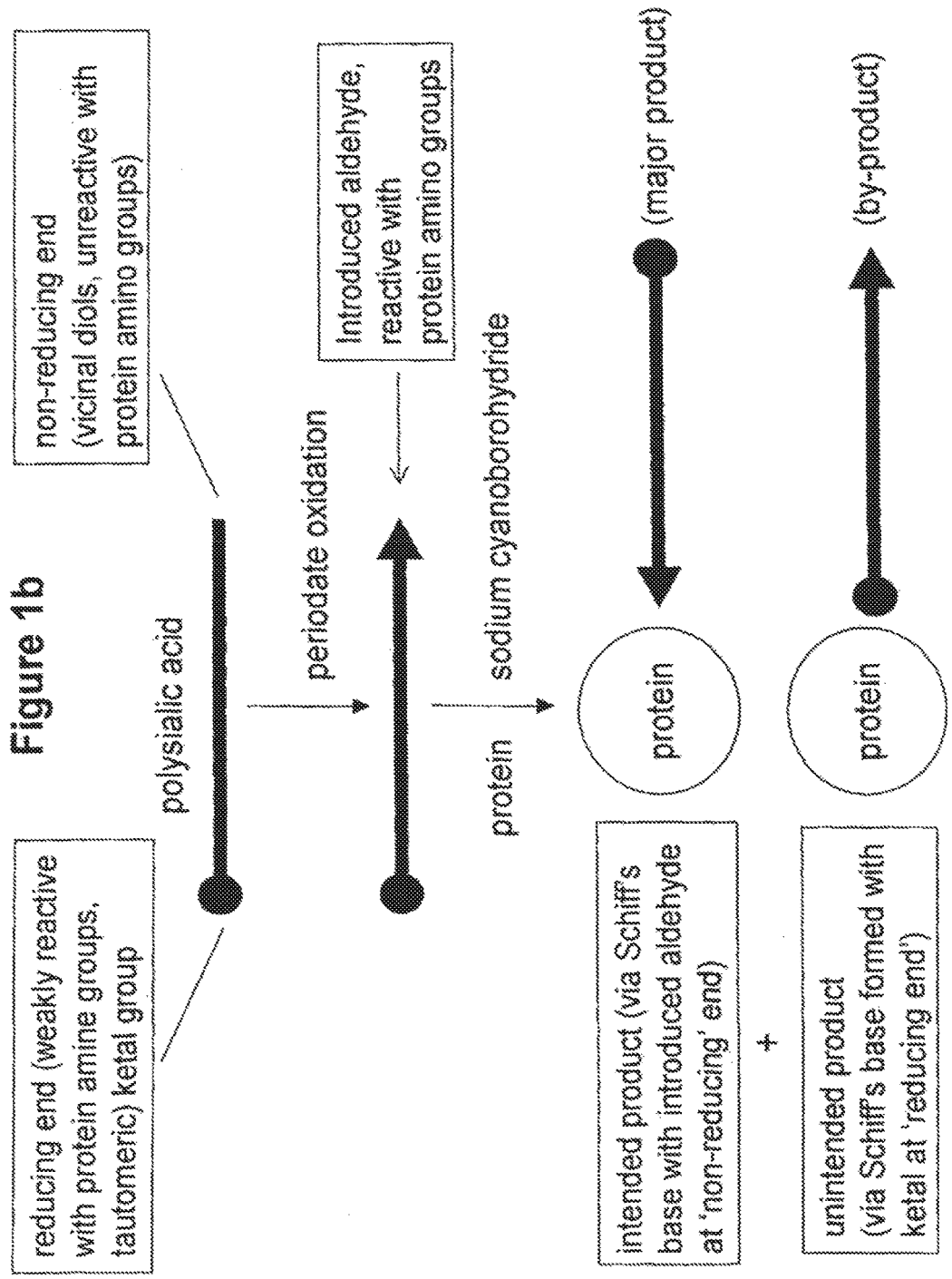

1) 18.7 KDa broad dispersed CA
2) 32.2 KDa CA from IEC
3) 32.2 KDa ultrafiltered CA
4) 32.2 KDa post oxidation CA
5) 40.9 KDa CA from IEC
6) 40.9 KDa ultrafiltered CA
7) 49.0 KDa post oxidation CA 4-20% Tris-Glycine Gel; run at 50 V/cm, 30µg CA per well 525 500 475 450 425 400 375 350 300 250 200 [NaCl] mM fractions
in 50mM (EtOH)3N buffer, pH 7.4

CA 39 (kDa, B)

FRACTIONATION OF CHARGED POLYSACCHARIDE

This application is a continuation of U.S. patent application Ser. 14/924,634, filed Oct. 27, 2015, which is a continuation of U.S. patent application Ser. 14/155,754 filed Jan. 15, 2014, which is a continuation of U.S. patent application Ser. 11/660,133, filed Aug. 28, 2007, which is the national phase entry of International Patent Application PCT/GB2005/003149, filed Aug. 12, 2005, which claims priority to International Patent Application PCT/GB2004/003511, filed Aug. 12, 2004 and European Patent Application 05251016.1 filed Feb. 23, 2005. The content of each of these applications is hereby incorporated by reference in its entirety.

The present invention relates to fractionation of polydisperse and charged polysaccharides optionally having reactive groups, into low polydispersity fractions (preferably pd <1.1). The fractionated polysaccharides are useful for conjugation to substrates such as peptides, proteins, drugs, drug delivery systems (e.g. liposomes), viruses, cells, (e.g. animal cells, microbes, synthetic polymers etc), or for use as excipients or diluents in pharmaceutical compositions.

Polysialic acids (PSAs) are naturally occurring unbranched polymers of sialic acid, produced by certain bacterial strains and mammals in certain cells [Roth et. al., 1993]. PSAs can be produced in various degrees of polymerisation: from n=about 80 or more sialic acid residues down to n=2 by either limited acid hydrolysis, digestion with neuraminidases or by is fractionation of the natural, bacterially or cell derived forms of the polymer.

The composition of different PSAs also varies such that there are: I. homopolymeric forms i.e. the alpha-2,8-linked PSA comprising the capsular polysaccharide of *E. coli* strain K1 and of the group-B meningococci, which is also found on the embryonic form of the neuronal cell adhesion molecule (N-CAM). II. Heteropolymeric forms, such as the alternating alpha-2,8 alpha-2,9 PSA of *E. coli* strain K92 and the group C polysaccharides of *N. meningitidis*. In addition, III. alternating copolymers containing sialic acids monomers other than sialic acid such as group W135 or group Y of *N. meningitidis*. PSAs have important biological functions including the evasion of the immune and complement systems by pathogenic bacteria and the regulation of glial adhesiveness of immature neurons during foetal development (wherein the polymer has an anti-adhesive function) [Muhlenhoff et. al., 1998; Rutishauser, 1989; Troy, 1990, 1992; Cho and Troy, 1994]. There are no known receptors for PSAs in mammals. The alpha-2,8-linked PSA of *E. coli* strain K1 is also known as 'colominic acid' (CA) and is used (in various lengths) to exemplify the present invention.

The alpha-2,8 linked form of PSA, among bacterial polysaccharides, is uniquely non-immunogenic (eliciting neither T-cell or antibody responses in mammalian subjects) even when conjugated to immunogenic carrier protein, which may reflect its existence as a mammalian (as well as a bacterial) polymer. Shorter forms of the polymer (up to n=4) are found on cell-surface gangliosides, which are widely distributed in the body, and are believed to effectively impose and maintain immunological tolerance to PSA. In recent years, the biological properties of PSAs, particularly those of the alpha-2,8 linked homopolymeric PSA, have been exploited to modify the pharmacokinetic properties of protein and low molecular weight drug molecules [Gregoriadis, 2001; Jain et. al., 2003; U.S. Pat. No. 5,846,951; WO-A-0187922]. PSA derivatisation of a number of therapeutic proteins including catalase and asparaginase [Fernandes and Gregoriadis, 1996 and 1997] gives rise to dramatic improvements in circulating half-life, and also allows such proteins to be used in the face of pre-existing antibodies raised as an undesirable (and sometimes inevitable) consequence of prior exposure to the therapeutic protein [Fernandes and Gregoriadis, 2001]. In many respects, the modified properties of polysialylated proteins are comparable to proteins derivatised with polyethylene glycol (PEG). For example, in each case, half-lives are increased, and proteins and peptides are more stable to proteolytic digestion, but retention of biological activity appears to be greater with PSA than with PEG [Hreczuk-Hirst et. al., 2002]. Also, there are questions about the use of PEG with therapeutic agents that have to be administered chronically, as PEG is only very slowly biodegradable [Beranova et. al., 2000] and high molecular weight forms tend to accumulate in the tissues [Bendele, et. al., 1998; Convers, et. al., 1997]. PEGylated proteins have been found to generate anti PEG antibodies that could also influence the residence time of the conjugate in the blood circulation [Cheng et. al., 1990]. Despite the established history of PEG as a parenterally administered polymer conjugated to therapeutics, a better understanding of its immunotoxicology, pharmacology and metabolism will be required [Hunter and Moghimi, 2002; Brocchini, 2003]. Likewise there are concerns about the utility of PEG in therapeutic agents that require high dosages, (and hence ultimately high dosages of PEG), since accumulation of PEG may lead to toxicity. The alpha 2,8 linked PSA therefore offers an attractive alternative to PEG, being an immunologically 'invisible' biodegradable polymer which is naturally part of the human body, and that can degrade, via tissue neuraminidases, to the non-toxic saccharide, sialic acid.

Our group has described, in previous scientific papers and in granted patents, the utility of natural PSAs in improving the pharmacokinetic properties of protein therapeutics [Gregoriadis, 2001; Fernandes and Gregoriadis, 1996, 1997, 2001; Gregoriadis et. al., 1993, 1998, 2000; Hreczuk-Hirst et. al., 2002; Mital, 2004; Jain et. al., 2003, 2004; U.S. Pat. No. 5,846,951; WO-A-0187922]. Now, we describe new derivatives of PSAs, which allow new compositions and methods of production of PSA-derivatised proteins (and other forms of therapeutic agents).

Methods have been described previously for the attachment of polysaccharides to therapeutic agents such as proteins [Jennings and Lugowski, 1981; U.S. Pat. No. 5,846,951; WO-A-0187922]. Some of these methods depend upon chemical derivatisation of the 'non-reducing' end of the polymer to create a protein-reactive aldehyde moiety (FIG. 1, 2). The reducing end of PSA (and other polysaccharides) is only weakly reactive with proteins under the mild conditions necessary to preserve protein conformation and the chemical integrity of PSA during conjugation. The non-reducing end of the sialic acid terminal unit, which contains vicinal diols, can be readily (and selectively) oxidised with periodate to yield a mono-aldehyde derivative. This derivative is much more reactive towards proteins and comprises of a suitably reactive element for the attachment of proteins via reductive amination and other chemistries. We have described this previously in U.S. Pat. No. 5,846,951 and WO-A-0187922. The reaction is illustrated in FIGS. 1a and 2 in which;

1a) shows the oxidation of CA (alpha-2,8 linked PSA from *E. coli*) with sodium periodate to form a protein-reactive aldehyde at the non-reducing end of the terminal sialic acid and 2) shows the selective reduction of the Schiff's base with sodium cyanoborohydride (NaCNBH$_3$) to form a stable irreversible covalent bond with the protein amino group.

The weak reactivity of the reducing end can be exploited to beneficial effect (by destroying the non-reducing end, capping the reducing end and derivatising with a bifunctional crosslinker), thus avoiding the product complexity described in FIG. 1b using the established method (FIG. 1a) of reductive amination of proteins with periodate oxidised CA.

Commercially available polymers (especially natural polymers, e.g. colominic acid (CA); used in most of the above papers) are produced from bacteria and are highly polydisperse. They may also contain bacterial contaminants such as endotoxins, salts etc. Such materials might not be suitable for the production of PSA-derivatised therapeutic agents intended for use in humans and animals, where the chemical and molecular definition of drug entities is of major importance because of the safety requirements of medical ethics and of the regulatory authorities (e.g. FDA, EMEA).

Therefore, we have solved the above problems by developing new methods for the fractionation of a polydisperse polysaccharide preparation into a series of low polydispersity (<1.1 pd) fractions each containing species within a narrow range of molecular weights. These new preparations are particularly suitable for the production of PSA-derivatised therapeutic agents intended for use in humans and animals, where the chemical and molecular definition of drug entities (e.g. predictable half-life) is of major importance because of the safety requirements of medical ethics and of the regulatory authorities (e.g. FDA, EMEA).

Ion exchange chromatography methods are well known in the art for separation of complex mixtures. In general the prior art uses variation in ionic strength to achieve this separation. In a solution of fully dissaciated electrolytes the ionic strength (I) is defined as $I=0.5 \Sigma_i C_i Z_i^2$, in which $C_i$ is the concentration of a particular ion, and $Z_i$ is the charge number of the ionic species.

Constantino et. al., [1999] have reported a chromatographic method suitable for the isolation of the high molecular weight fraction from a polydisperse preparation of a negatively charged polysaccharide such as the *Haemophilus influenzae* type b and *Neissera meningitidis* group A and group C antigens. The material obtained still contains species with a large range of molecular weights (i.e. it is still highly polydisperse) but it is free from small oligosaccharides. The removal of the oligosaccharides makes this material more suitable for use in polysaccharide based vaccines. The removal of the low molecular weight species was accomplished, using a two step elution process. Briefly Hib (*Haemophilus influenzae* type b antigen), a negatively charged polysaccharide, was bound to an ion exchange resin and the low is molecular weight species where eluted by extensive washing with a low ionic strength buffer. The intermediate and high molecular weight species, which remain bound in the column were recovered by eluting with a high ionic strength buffer.

Zhang et al (1997) have reported use of high performance ion exchange chromatography for the separation of colominic acid polymers. Three stock solutions are mixed together to form a linear gradient which has a progressively higher concentration of sodium nitrate.

The present invention may be distinguished over the disclosures of Constantino et al and Zhang et al by its use of a step rather than a linear gradient elution. Constantino et al use a large volume of low ionic strength wash to remove all low molecular weight species from the column and then a high volume high ionic strength wash to remove all other species from the column. This does not result in separation into low polydispersity fractions. The use of a step gradient according to the present invention, with steps that differ only slightly in ionic strength, leads to the isolation of low polydispersity fractions.

Ravenscroft et. al., [1999] have developed a procedure for the molecular weight determination of low molecular weight Hib oligosaccharides using ion exchange chromatography (IEC). Ion exchange affords excellent resolution of small oligosaccharides with DP (degree of polymerisation) values of 10 or lower. This was exploited to separate a mixture of oligomers using ion exchange into individual oligomers. The DP was measured with mass-spectroscopy and the purified oligosaccarides were then used as standards to calibrate an ion exchange column enabling thus the determination of the molecular weight of small oligosaccharides to be carried out using analytical ion exchange.

The present invention generates fractions of polysaccharides of low polydispersity in good yield which may be used to provide pharmaceutically useful protein-polymer conjugates. None of the prior art describe techniques which fractionate polysaccharides in this manner.

According to the invention there is provided a process for separating polydisperse ionically charged polysaccharide into fractions of different average molecular weight in which an aqueous solution of the polydisperse polysaccharides is contacted with ion exchange resin in a column, the polysaccharides are then subjected to selective elution by aqueous elution buffer, and polysaccharide is recovered from eluted fractions, characterised in that the selective elution involves washing the resin in the column sequentially with at least three elution buffers each having different and constant ionic strength and/or pH and in which the second and subsequent buffers have higher ionic strength and/or pH than the buffers of the immediately preceding step.

In the process, preferably the elution buffers all have the same pH, but have successively higher ionic strength due to increasing concentrations of ions such as ions of salts of strong mineral acids and strong mineral bases. Preferably the salt is sodium chloride. Preferably the increase in ionic strength is the same as that produced by increasing the NaCl concentration by 5-100 mM, preferably 25 mM. This corresponds to an increase in ionic strength of 0.005 to 0.1M, preferably 0.025M.

Alternatively, the elution buffers may have successively higher pH values. Preferably, the difference between the pH of each eluent is the same and preferably 0.2 pH units. The pH of each buffer preferably lies in the range 7.4-13. Typically, the first elution buffer will have a pH of around 7.4 and at least 5 elution steps will be used in the process. Ideally, the ionic strength of all elution buffers will be less than 25M. The concentration of hydrogen and hydroxyl ions in the buffers is so low that their contribution to the total ionic strength of the solution is negligible.

An increase in ionic strength and pH may be used in tandem in the fractionation process. Alternatively, pH elution may be used initially in a series of steps to raise the pH from 7.4 to at least 8.8, and then ionic strength elution may begin. As an alternative, increasing the pH after a short salt gradient may be performed, but this requires a starting pH of greater than 7.4. A low pH range (around 4) may allow fractionation when using a strong ion exchange column. However, since many polysaccharides are not stable at this pH, the pH of the eluted fractions should in this case immediately be adjusted to around 7.4.

Preferably, the elution buffers contain a base, which is preferably triethonolamine.

It is possible for there to be an initial washing step, in which a low ionic concentration elution buffer is washed through the column. For instance such an initial wash step may be carried out with a buffer having a salt concentration more than 100 mM lower in salt concentration than the first of the essential three elution buffers used in the process. Such an initial step may wash out low molecular weight contaminants or other contaminants which are by-products from recovery processes for naturally occurring materials. Such an initial wash step may involve a volume of at least 1, preferably at least 1.5 column volumes, based on the volume of the ion exchange resin column. It is to be noted that a column of ion exchange resin may have a diameter of the cross-section which is greater than the height or may, as in a conventional column, have a height which is greater than the diameter of the cross section. The volume may be in the range 1 to 5000 mL. The height of the column may be in the range 1 cm to 5000 $cm^2$. The cross sectional area may be in the range 1 cm to 5000 $cm^2$. The cross section may be of any shape but is preferably round.

We have found that it is preferred for each of the essential elution steps to use at least 1.0, preferably at least 1.25 and most preferably at least 1.5 column volumes of the respective elution buffer. Preferably no more than 3 column volumes of elution buffer are used. The flow rate for a 75 ml matrix is preferably 7 ml/minute.

The process of the invention preferably comprises at least 5, for instance as many as 20 or, generally in the range 6 to 12, sequential steps of elution with the elution buffers of successively increasing ionic strength. The ionic strength in the first of these essential steps is generally in the range 1 mM to 1M. Weaker ionic concentrations will be required for stronger counterions, such as sulphate, than for chloride.

Preferably the ionic strength of an elution buffer is varied by varying the level of a salt of a strong mineral acid and a strong mineral base, preferably sodium chloride.

With regard to the recovery steps, these generally involve steps in which the polysaccharide is isolated from the salt, for instance using membranes, for instance ultra-filtration membranes. Such steps may allow concentration of the polysaccharides to form more highly concentrated solutions. Such solutions may be subjected to additional steps of membrane treatment, for instance successive ultra-filtration or other filtration steps. The elution buffer may contain a volatile acid or base and in this case the recovery involves volatilisation of the volatile acid or base from the eluted fractions. Although it is possible to recover the polysaccharide from aqueous solutions by precipitation techniques, for instance involving non solvents for the polysaccharides, it is preferred that no such solvents are utilised, since this may make final isolation from the respective solvents more difficult. Consequently the final step of recovery preferably involves evaporation of the water and, preferably, any remaining volatile buffer components remaining from the elution steps. In a preferred case wherein triethanolamine is present, both the triethanolamine cation and acetate anion are volatile and can easily be removed under vacuum.

The polysaccharide may be finally isolated from solution by drying, preferably under reduced pressure. This is preferably performed by freeze-drying.

Precipitation, preferably using a non solvent, may be carried out as a preliminary step to fractionation to remove a portion of the population and decrease polydispersity of the higher molecular weight fractions. Preferably, differential ethanol precipitation is used.

The invention described herein is the use of a step gradient strategy, which affords the stepwise removal (and subsequent collection) of progressively higher molecular weight species from a polydisperse polymer population bound to an ion exchange resin. The ion exchange resin may be any strong or weak anion or cation exchange medium. Using a wash of any given ionic strength will elute a complex population of species from the column. By using a series of short washes in tandem, each step elutes a part of the population that would be eluted by the next step, so at each point only a small population is actually eluted, facilitating the fractionation of the polydisperse preparations into fractions with narrow polydispersity. This process may also facilitate removal of impurities e.g. salt, endotoxin etc.

In IEC, molecules do not remain absolutely motionless at low salt concentrations. They move extremely slowly as bands. Their speed depends upon the binding constant of a molecule to the column, which varies with the ionic strength. When the binding constant is, for example, medium, a band will move relatively slowly through the column and broaden to some extent. When the binding constant is weak the band will move very quickly but with negligible broadening. When the binding constant is strong the band will move very slowly, mostly by broadening. A linear gradient prevents the broadening, giving narrow bands and well-defined peaks. A step gradient on the other hand elutes the molecules which at the particular concentration have a low binding constant as a tight band and elutes those which have an intermediate binding constant as a diffuse band (which is likely to carry over into the next fraction). Molecules which have a high binding constant will exhibit little movement and they will mostly be broad. The result is that each step produces a peak that rises very rapidly and then slowly declines producing a tail. Step gradients are well documented to behave in this manner. The rise of the peak contains more of the species with a low binding constant and the tail contains more of the species with the intermediate binding constant (which will also carry over to the next fraction). The longer each step runs for, the more it causes the species which have an intermediate binding constant to broaden and eventually some are eluted, enriching what is left in the column of higher species. So a step gradient also elutes species, which in a linear gradient would come down at higher ionic strength and cause some shifting of even the much higher bands. Although this does not facilitate resolution, it is advantageous to fractionation. If two species have a very close binding constant a step gradient can afford purification or enrichment of the species with the higher binding constant. The first step elutes both species, but preferentially the one with the lower binding constant more. The second step elutes both species but since most of the low binding constant species has already been removed in the previous step, most of the fraction is the high binding constant species. So a step gradient, though it cannot completely separate species with similar binding constants, can result in significant enrichment of the one with the higher binding constant.

Taking CA as an example, the binding constant is the result of the average charge on the molecule. The difference in binding constants depends on the charge difference between different species. The charge ratio between a species with 41 charges and a species with 40 charges is a lot lower than that between a species with 11 charges and one with 10 charges. As the amount of charges (and hence)

monomers increases the difference between the binding constants decreases. At larger molecular weights it becomes practically negligible.

A linear gradient therefore results in good resolution for the low molecular weight species, but as the molecular weight (and hence the charge) increases, resolution decreases. The step gradient strategy, in contrast, elutes more of the lower than higher molecular weight species with each wash. Thus the step gradient produces less disperse fractions towards the higher end of the molecular weight range and more disperse fractions in the middle and beginning of the range.

Several parameters may affect the separation.
1) pH: The charge on the polymer is pH dependent; decreasing the pH will reduce the charge and might afford better resolution on the higher end of the molecular weight range.
2) Step wash volume: The more washing the less of the higher molecular weight species would be recovered, but the lower their polydispersity.
3) Number of steps: The number of steps is also an important parameter. Skipping the early steps may result in a decrease on the average size obtained in each fraction and an increase in polydispersity that becomes less and less pronounced as the molecular weight increases. If more steps are used it may increase the resolution of most fractions, but it will decrease the average amount of CA in each fraction.
4) Temperature. Lower temperature increases the strength of binding and may decrease the size of species coming down in each fraction.

In the invention the polydisperse polysaccharide may be a naturally occurring polysaccharide, a hydrolysis product thereof or a functionalised derivative of either of these. The invention is of particular utility in separating naturally occurring polysaccharides such as bacterial polysaccharides, for instance polysaccharide antigens. The invention is of particular utility in separating sialic-acid polymers and copolymers, for instance poly(2,8-linked sialic acid), poly (2,9-linked sialic acid) or an alternating 2,8-2,9-linked PSA. Preferably the polysaccharide is colominic acid (CA) or an oxidised, reduced, aminated and/or hydrazide derivative thereof.

The polydispersity of molecular weight (that is the weight average molecular weight divided by the number average molecular weight) of the polydisperse polysaccharide should be at least 1.1, preferably at least 2.0. We have found that the process has particular utility where the weight average molecular weight of the polydisperse polysaccharide is at least 1 kDa, preferably at least 10 kDa, and preferably at least 100 kDa.

The process is of use for producing very low polydispersity polysaccharide fractions. For instance the product polysaccharide recovered from the eluted fractions preferably has polydispersity less than 1.5, most preferably less than 1.25, for instance 1.1 or even lower. We have found it possible to achieve polydispersities down to around 1.01.

Preferably the polysaccharide starting material has at least 1, more preferably at least 5, more preferably at least 10, for instance at least 50, saccharide units. Preferably the polysaccharide is polysialic acid (PSA) comprising sialic acid units linked a (2,8) or a (2,9) to one another.

There is no particular upper limit on the size of polydisperse polysaccharides to be fractionated. In the case of PSA, however, we find that most polymers of utility have a weight average molecular weight of up to 150 kDa.

The PSA may be derived from any source, preferably a natural source such as a bacterial source, e.g. *E. coli* K1 or K92, group *B. meningococci*, or even cow's milk or N-CAM. The sialic acid polymer may be a heteropolymeric polymer such as group 135 or group V of *N. meningitidis*, or may be synthesised. The PSA may be in the form of a salt or the free acid. It may be in a hydrolysed form, such that the molecular weight has been reduced following recovery from a bacterial source. The PSA may be material having a wide spread of molecular weights such as having a polydispersity of more than 1.3, for instance as much as 2 or more. Preferably the polydispersity of molecular weight is less than 1.2, for instance as low as 1.01.

The following description describes the preferred embodiments of the process of the present invention carried out on the polysaccharide PSA for which the invention is of particular utility.

A population of PSAs having a wide molecular weight distribution may be fractionated into fractions with lower polydispersities, i.e. into fractions with differing average molecular weights. Fractionation is preferably anion exchange chromatography, using for elution a suitable basic buffer. When the polysaccharide has carboxylic acid groups then anion exchange is particularly desirable. We have found a suitable anion exchange medium; a preparative medium such as a strong ion exchange material based on activated agarose, having quaternary ammonium ion pendant groups (ie strong base). The choice of medium will be dependent upon whether pH or ionic strength is the means for fractionation, and will be apparent to a person skilled in the art. The elution buffer is non-reactive and is preferably volatile so that the desired product may be recovered from the base in each fraction by evaporation. Suitable examples are amines, such as triethanolamine. Recovery may be by freeze-drying for instance. The fractionation method is suitable for a PSA starting material as well as its derivatives. The technique may thus be applied before or after the essential process steps on related inventions described in PCT/GB04/03488, application filed even date herewith (agent's ref: HMJ03917) and application filed even dated herewith (agent's ref: HMJ03871), in which we describe various derivatisation reactions carried out on polysialic acids and intermediates formed therein.

It is believed this is the first time IEC has been applied to fractionate ionic polysaccharides with molecular weights above about 5 kDa, especially PSA of such molecular weights.

According to a further aspect of this invention there is provided a process for fractionating a population of ionic polysaccharide with a molecular weight higher than 5 kDa using IEC using in the elution buffer a base or acid which is preferably volatile.

Preferably the polysaccharide has carboxylic acid groups and the ion exchange is anion exchange. Preferably the elution buffer contains an amine, more preferably triethanolamine. Most preferably the polysaccharides are recovered from the fractions by drying, preferably under reduced pressure, most preferably freeze-drying.

This method can be applied for the fractionation of CA having reactive moieties which are stable in water (maleimide or iodoacetate etc.) and other natural (e.g. dextran sulphate) and synthetic (e.g. polyglutamic acid, polylysine, hyaluronic acid) charged polymers. Cation and anion exchange chromatography can also be used for fractionation of charged polymers using salt or pH gradient.

It is believed that it is also the first time that IEC has been used to separate ionic polysaccharides in combination with precipitation techniques and/or ultrafiltration methods.

The IEC method may remove by products such as endotoxins which remain in the commercially available PSAs and CAs.

Ion pair and hydrophobic interaction chromatography can also be used for fractionation of polymers and protein-polymer conjugates.

In the invention there is provided a new process for producing a series of narrow polydispersity (pd <1.1) preparations (fractions) of a polysaccharide, preferably PSA compound (native or activated), in which the high polydispersity, negatively charged starting material is bound to an anion exchange resin and the fractions are eluted with a series short washes each with a progressively higher ionic strength.

In an alternative embodiment, +ve and –ve charged broad disperse polymers and protein-polysaccharide conjugates can be fractionated by cation or anion exchange chromatography respectively.

According to an another aspect of the invention there is provided a new process in which a polysialylated macromolecule, where the product is polydisperse owing to the polydispersity of the polysialic acid starting material conjugated to the macromolecule, is fractionated into narrow polydispersity preparations using the same IEC and step gradient strategy as described above.

In the process the parameters (e.g. amount of matrix used, amount of sample loaded, temperature, flow rate, gradients etc.) are preferably optimized for fractionation of a polysialylated macromolecule (for instance), where the product is polydisperse owing to the polydispersity of the PSA starting material conjugated to the macromolecule, is fractionated into narrow polydispersity preparations using the same IEC and step gradient strategy as described above. These steps are carried out under conditions such that there is substantially no mid-chain cleavage of the backbone of a long-chain (polymeric) starting material, that is no substantial molecular weight reduction should occur.

The narrow dispersed polysaccharides can be used to generate active groups. For instance aldehyde groups are suitable for conjugating to amine-group containing substrates or hydrazine compounds. Processes in which the activated product of an oxidation step is subsequently conjugated to substrate compound are described. Preferably the conjugation reaction (as described in our earlier publications mentioned above) involves conjugation of PSA with an amine to form a Schiff base, preferably followed by reduction to form a secondary amine moiety. The process is of particular value for derivatising proteins, of which the amine group is suitably the epsilon amine group of a lysine group or the N-terminal amino group. The process is of particular value for derivatising protein or peptide therapeutically active agents, such as cytokines, growth hormones, enzymes, hormones, antibodies or fragments. FIGS. 1 and 2 show reaction schemes for such reactions, wherein the polysaccharide is PSA.

Alternatively the process may be used to derivatise drug delivery systems, such as liposomes, for instance by reacting the aldehyde with an amine group of a liposome forming component. Other drug delivery systems are described in our earlier case U.S. Pat. No. 5,846,951. Other materials that may be derivatised include viruses, microbes, cells, including animal cells and synthetic polymers.

Alternatively the substrate may have a hydrazine group, in which case the product is a hydrazone. This may be reduced if desired, for additional stability, to an alkyl hydrazide.

The derivatisation of proteins and drug delivery systems may result in increased half life, improved stability, reduced immunogenicity, and/or control of solubility and hence bioavailability and pharmaco-kinetic properties, or may enhance solubility actives or viscosity of solutions containing the derivatised active.

Preferably the polysaccharide compounds recovered from eluted fractions comprise sialic acid units, most preferably consist of sialic acid units. More preferably the polysaccharides have 1-1000 sialic acid units, for instance 10-500, more preferably 10 to 50 sialic acid units. The eluted fractions may consist of monomers, dimers, or larger polymers. Preferably, the polydispersity of a fraction will be less than 1.26, ideally less than 1.2, and ideally in the range 1.01 to 1.10.

It is believed that this is the first time that a polysialic aid, particularly CA, having a polydispersity of molecular weight of less than 1.26 has been isolated. Accordingly, a further aspect of the present invention provides a polysialic acid having a polydispersity of molecular weight of less than 1.26, preferably no more than 1.2, most preferably in the range 1.01 to 1.10. The polysialic acid may be CA, or an oxidised, reduced, aminated and/or hydrazide derivative thereof. Preferably, the polysialic acid has a molecular weight of at least 5 kDa, preferably at least 10 kDa.

The fractionation process that we described here is linearly scalable and reproducible. It is suitable for industrial scale production and for control of polydispersity of CA. The fractionation technology, described here, allows for fractionation of CA as well as other polysaccharide (preferably charged), protein-polymer conjugates and vaccines to be prepared with a homogenous (monodispersed) polymer chain length.

FIG. 1b is a reaction scheme showing preparation of products using original conjugation methods;

The invention is illustrated further in the accompanying examples.

EXAMPLES

Materials

Ammonium carbonate, ethylene glycol, PEG (8 KDa), sodium cyanoborohydride (>98% pure), sodium meta-periodate, triethanolamine, sodium chloride, sodium nitrate, sodium azide, PBS tablets and molecular weight markers were obtained from Sigma Chemical Laboratory, UK. The CA used, linear alpha-(2→8)-linked E. coli K1 PSAs (22.7 kDa average, high polydispersity 1.34; 39 kDa, p.d. 1.4; 11 kDa, p.d. 1.27) was from Camida, Ireland, Other materials included 2,4 dinitrophenyl hydrazine (2,4 DNPH) (Aldrich Chemical Company, UK), dialysis tubing (3.5 kDa and 10 kDa cut off limits; Medicell International Limited, UK), Sepharose SP HiTrap, PD-10 columns (Pharmacia, UK), Tris-glycine polyacrylamide gels (4-20%), Tris-glycine sodium dodecylsulphate running buffer and loading buffer (Novex, UK), Sepharose Q FF and DEAE (Amersham Biosciences, UK), Tris-Borate-EDTA (TBE) polyacrylamide gels (4-20% and 20%), TBE buffer and loading buffer (Invitrogen, UK). Deionised water was obtained from an Elgastat Option 4 water purification unit (Elga Limited, UK). All reagents used were of analytical grade. A plate reader (Dynex Technologies, UK) was used for spectrophotometric determinations in protein or CA assays.

Methods

Protein and Colominic Acid Determination

Quantitative estimation of PSAs (as sialic acid) was carried out by the resorcinol method [Svennerholm 1957] as described elsewhere [Gregoriadis et. al., 1993; Fernandes and Gregoriadis, 1996, 1997]. Protein was measured by the bicinchoninic acid (BCA) colorimetric method.

Example 1

Preparation of Monofunctional PSA

1a Activation of CA

Figure 1A:
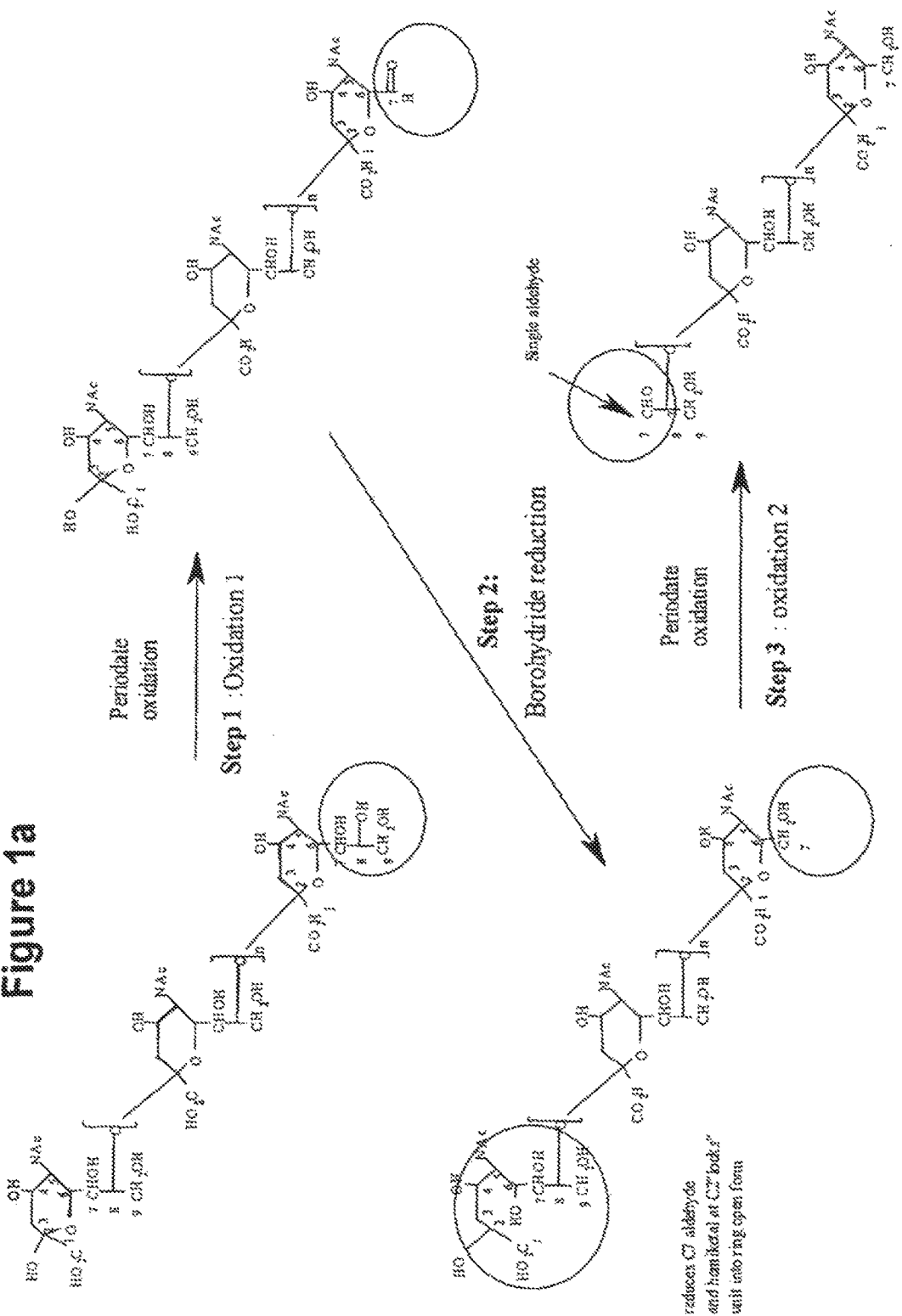
FIG. 1a is a reaction scheme showing preparation of monofunctional CA.
Figure 2:
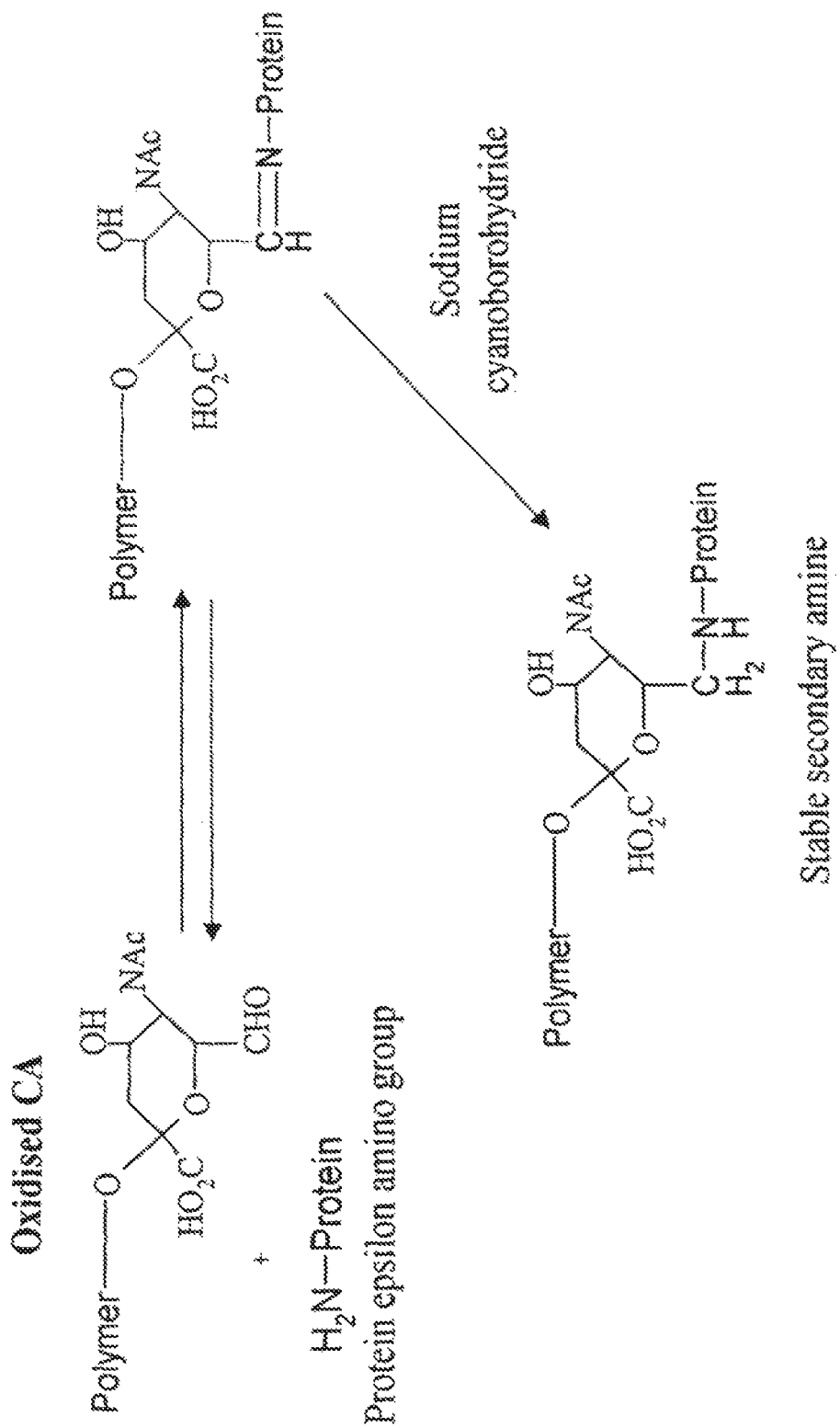
FIG. 2 is a reaction scheme showing preparation of protein-CA conjugates.

Freshly prepared 0.02 M sodium metaperiodate ($NaIO_4$; 6 fold molar excess over CA) solution was mixed with CA at 20° C. and the reaction mixture was stirred magnetically for 15 min in the dark. The oxidised CA was precipitated with 70% (final concentration) ethanol and by centrifuging the mixture at 3000 g for 20 minutes. The supernatant was removed and the pellet was dissolved in a minimum quantity of deionised water. The CA was again precipitated with 70% ethanol and then centrifuged at 12,000 g. The pellet was dissolved in a minimum quantity of water, lyophilized and stored at −20° C. until further use (FIG. 1; step 1).

1b. Reduction of CA

Oxidised CA (CAO; 22.7 kDa) was reduced in presence of sodium borohydride. Freshly prepared 15 mM sodium borohydride ($NaBH_4$; in 0.1M NaOH diluted to pH 8-8.5 by diluting with dilute $H_2SO_4$ solution) was mixed with CAO (100 mg CA/ml) at 20° C. and the reaction mixture was stirred for up to 2 h in the dark. The pH was brought down to 7 by the completion of the reaction. The oxidised/reduced CA (CAOR) was dialysed (3.5 kDa molecular weight cut-off for dialysis tubing) against 0.01% ammonium carbonate buffer pH 7 at 4° C. Ultracentrifugation was used to concentrate the CAOR solution, from the dialysis tubing. The filtrate was lyophilized and stored at 4° C. until further required. The determination of any aldehyde content was determined as described under 'determination of CA oxidation' (FIG. 1; step 2).

1c Reoxidation of CA

After confirmation of no aldehyde content the CAOR was again oxidised as reported under activation of CA except CAOR was incubated with periodate solution for a longer time (up to 1 h). The degree of oxidation in the CAORO product was measured on lyophilized powder obtained from this stage as well (FIG. 1; step 3).

1d Determination of the Oxidation State of CA and Derivatives

Qualitative estimation of the degree of colominic acid oxidation was carried out with 2,4 DNPH, which yields sparingly soluble 2,4 dinitrophenyl-hydrazones on interaction with carbonyl compounds. Non-oxidised (CA), oxidised (CAO), reduced (CAOR) and re-oxidised (CAORO) (5 mg each), were added to the 2,4-DNPH reagent (1.0 ml), the solutions were shaken and then allowed to stand at 37° C. until a crystalline precipitate was observed [Shriner et. al., 1980]. The degree (quantitative) of CA oxidation was measured with a method [Park and Johnson, 1949 9 based on the reduction of ferricyanide ions in alkaline solution to ferric ferrocyanide (Persian blue), which is then measured at 630 nm. In this instance, glucose was used as a standard.

1e Preparation of $CA-NH_2$

CAO at (10-100 mg/ml) was dissolved in 2 ml of deionised water with a 300-fold molar excess of $NH_4Cl$, in a 50 ml tube and then $NaCNBH_3$ (5 M stock in 1 N NaOH(aq), was added at a final concentration of 5 mg/ml. The mixture was incubated at room temperature for 3 days. A control reaction was also set up with colominic acid instead of CAO. Product colominic acid amine derivative was precipitated by the addition of 5 ml ice-cold ethanol. The precipitate was recovered by centrifugation at 4000 rpm, 30 minutes, room temperature in a benchtop centrifuge. The pellet was retained and resuspended in 2 ml of deionised water, then precipitated again with 5 ml of ice-cold ethanol in a 10 ml ultracentrifuge tube. The precipitate was collected by centrifugation at 30,000 rpm for 30 minutes at room temperature. The pellet was again resuspended in 2 ml of deionised water and freeze-dried.

1f Assay for Amine Content

The TNBS (picrylsulphonic acid i.e. 2,4,6-tri-nitro-benzene sulphonic acid) assay was used to determine the amount of amino groups present in the product [Satake et. al., 1960]. In the well of a microtitre plate TNBS (0.5 µl of 15 mM TNBS) was added to 90 µl of 0.1 M borate buffer pH 9.5. To this was added 10 µl of a 50 mg/ml solution of CA-amide. The plate was allowed to stand for 20 minutes at room temperature before reading the absorbance at 405 nm. Glycine was used as a standard, at a concentration range of 0.1 to 1 mM. TNBS trinitrophenylates primary amine groups. The TNP adduct of the amine is detected. Testing the product purified with a double cold-ethanol precipitation using the TNBS assay showed close to 90% conversion.

1g Preparation of Maleimide Polymer (CA-M)

The CAORO synthesised in Example 1c above was reacted with 5 molar equivalents of N-[β-maleimidopropionic acid] hydrazide in 0.1 M sodium acetate for 2 h at 20° C. The product hydrazone was precipitated in ethanol, resuspended in sodium acetate and precipitated again in ethanol, redissolved in water and freeze-dried. The product is useful for site-specific conjugation to the thiol groups of cysteine moieties in proteins and peptides.

1h Gel Permeation Chromatography

Figure 3:
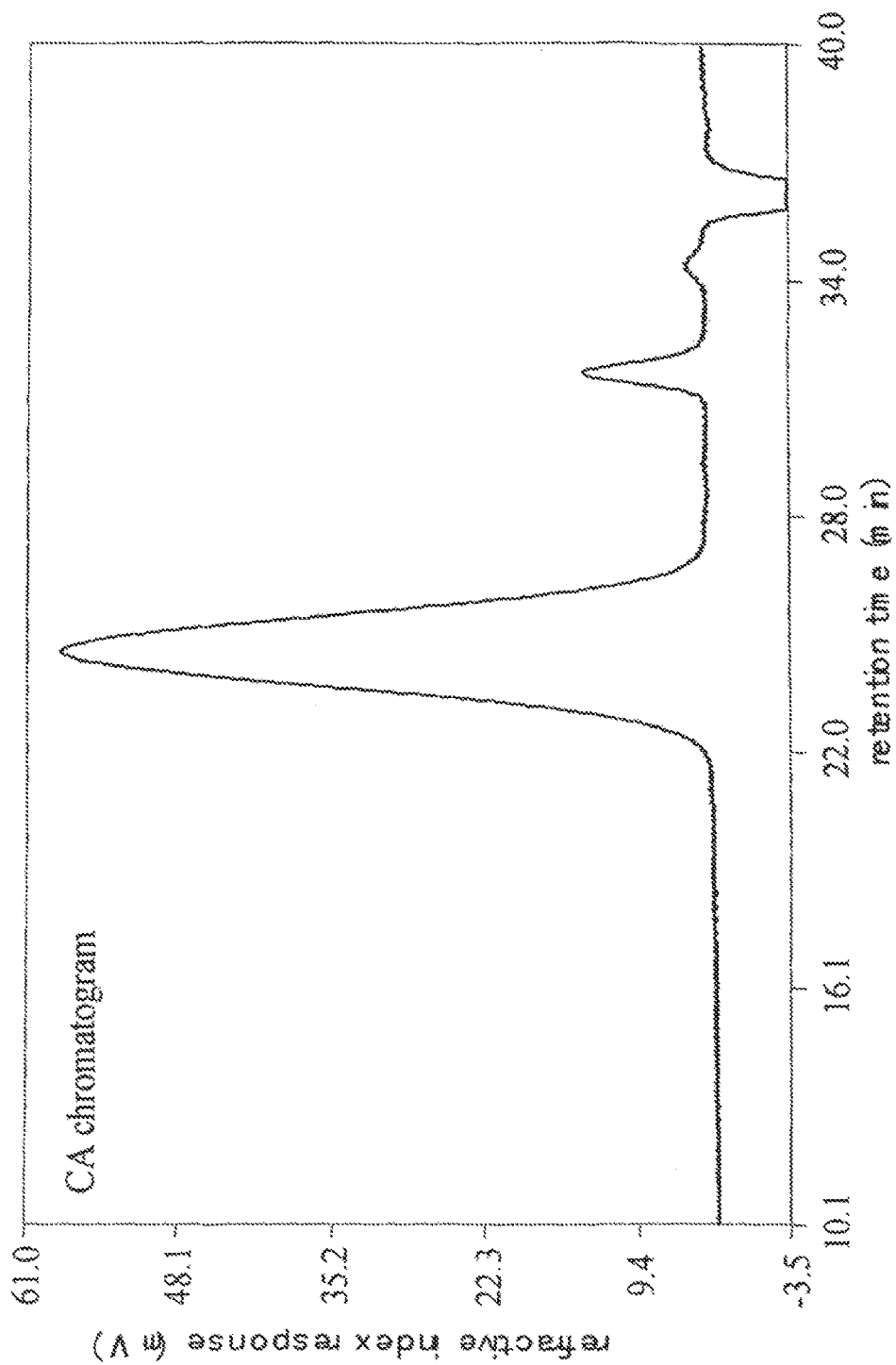
FIG. 3 shows the results of the Gel Permeation Chromatography of CA.

CA samples (CA, CAO, CAOR and CAORO) were dissolved in $NaNO_3$ (0.2M), $CH_3CN$ (10%; 5 mg/ml) and were chromatographed on over 2× $GMPW_{XL}$ columns with detection by refractive index (GPC system: VE1121 GPC solvent pump, VE3580 RI detector and collation with Trisec 3 software (Viscotek Europe Ltd). Samples (5 mg/ml) were filtered over 0.45 .mu.m nylon membrane and run at 0.7 cm/min with 0.2M $NaNO_3$ and $CH_3CN$ (10%) as the mobile phase (FIG. 3).

Results of Example 1

Preparation of Monofunctional PSA

The integrity of the internal alpha-2,8 linked Neu5Ac residues post periodate and borohydride treatment was analysed by GPC and the chromatographs obtained for the oxidised (CAO), oxidised reduced (CAOR), double oxidised (CAORO), amino CA (CA-NH2) materials were compared with that of native CA. It was found (FIG. 3) that oxidized (15 minutes) (CAO), reduced (CAOR), double oxidised (1 hr) (CAORO) and native CA exhibit almost identical elution profiles, with no evidence that the successive oxidation and reduction steps give rise to significant fragmentation of the polymer chain. The small peaks are indicative of buffer salts.

The results of quantitative assay of CA intermediates in the double oxidation process using ferricyanide were consistent with the results of qualitative tests performed with 2,4 DNPH which gave a faint yellow precipitate with the native CA, and intense yellow colour with the aldehyde containing forms of the polymer, resulting in an intense yellow precipitate after ten minutes of reaction at room temperature.

The amination content of the polymer was found to be 85% by the 2,4,6-tri-nitro-benzene sulphonic acid (TNBS) assay. The PSA aldehyde derivative could also be reacted with a linking compound having a hydrazide moiety and a N-maleimide moiety to form a stable hydrazone having an active maleimide functionally useful for reacting with a thiol group. The maleimide content of the polymer was found to be 95% by the maleimide assay.

Example 2

Fractionation of Colominic Acid by IEC (CA, 22.7 KDa, pd 1.34)

2.1 Fractionation at Large Scale

An XK50 column (Amersham Biosciences, UK) was packed with 900 ml Sepharose Q FF (Amersham Biosciences) and equilibrated with 3 column volumes of wash buffer (20 mM triethanolamine; pH 7.4) at a flow rate of 50 ml/min. CA (25 grams in 200 ml wash buffer) was loaded on column at 50 ml per minute via a syringe port. This was followed by washing the column with 1.5 column volumes (1350 ml) of washing buffer.

The bound CA was eluted with 1.5 column volumes of different elution buffers (Triethanolamine buffer, 20 mM, pH 7.4, with 0 mM to 475 mM NaCl in 25 mM NaCl steps) and finally with 1000 mM NaCl in the same buffer to remove all residual CA and other residues (if any). The flow rate was 7 ml/minute.

Figure 4:
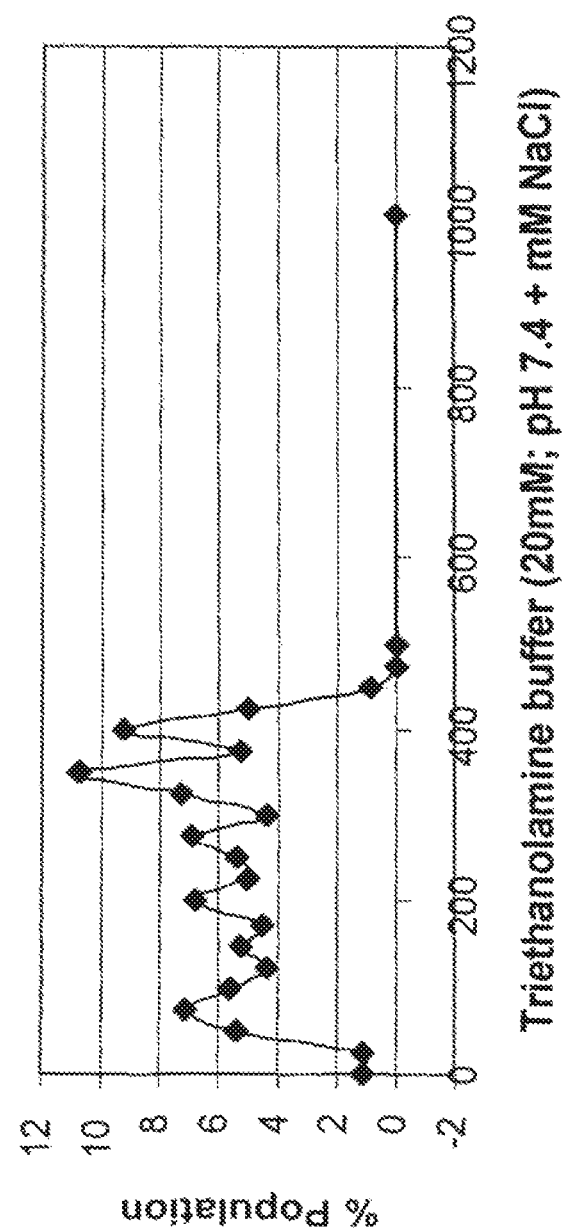
FIG. 4 shows % population of different CA fractions.

The samples were concentrated to 20 ml by high pressure ultra filtration over a 3-10 kDa membrane (Vivascience, UK). These samples were buffer exchanged into deionised water by repeated ultra filtration at 4° C. The samples were analysed for average molecular weight and other parameters by GPC (as reported in example 1h) and native PAGE (stained with alcian blue) [Table 1 and 2; FIG. 4, 5,6].

Example 2.2

Fractionation at Medium and Smaller Scale

The following samples were fractionated using an identical wash and gradient system on a smaller scale (1-75 ml matrix; 0.2-3 gram of colominic 10 acid): CA (CA, 22.7 kDa, pd 1.34; CA, 39 KDa, pd 1.4), CAO (CAO, 22.7 kDa, pd 1.34), monofunctional CAO (RO, 22.7 kDa; pd 1.34), CA-NH₂ (22.7 kDa, pd 1.34), CAM (as per example 1g) produced were monitored throughout.

Figure 7:
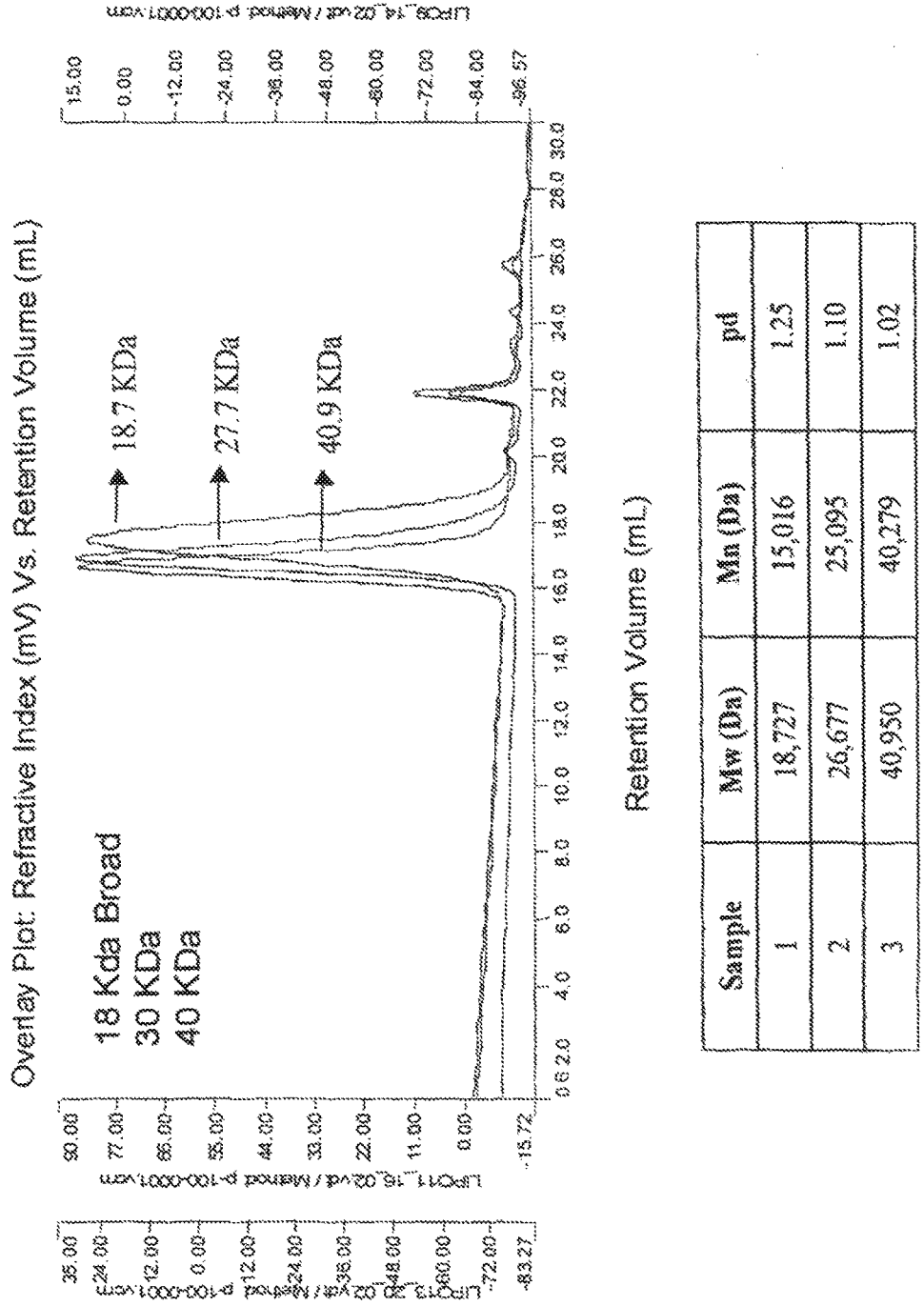
FIG. 7 shows a typical chromatogram for CA fractions.

Narrow fractions of CA produced using above procedure were oxidised is with 20 mM periodate and analysed by gel permeation chromatography (GPC) and native PAGE for gross alteration to the polymer (FIG. 7, 8).

Results of Example 2: Fractionation at Large, Medium and Small Scale

Figure 5:
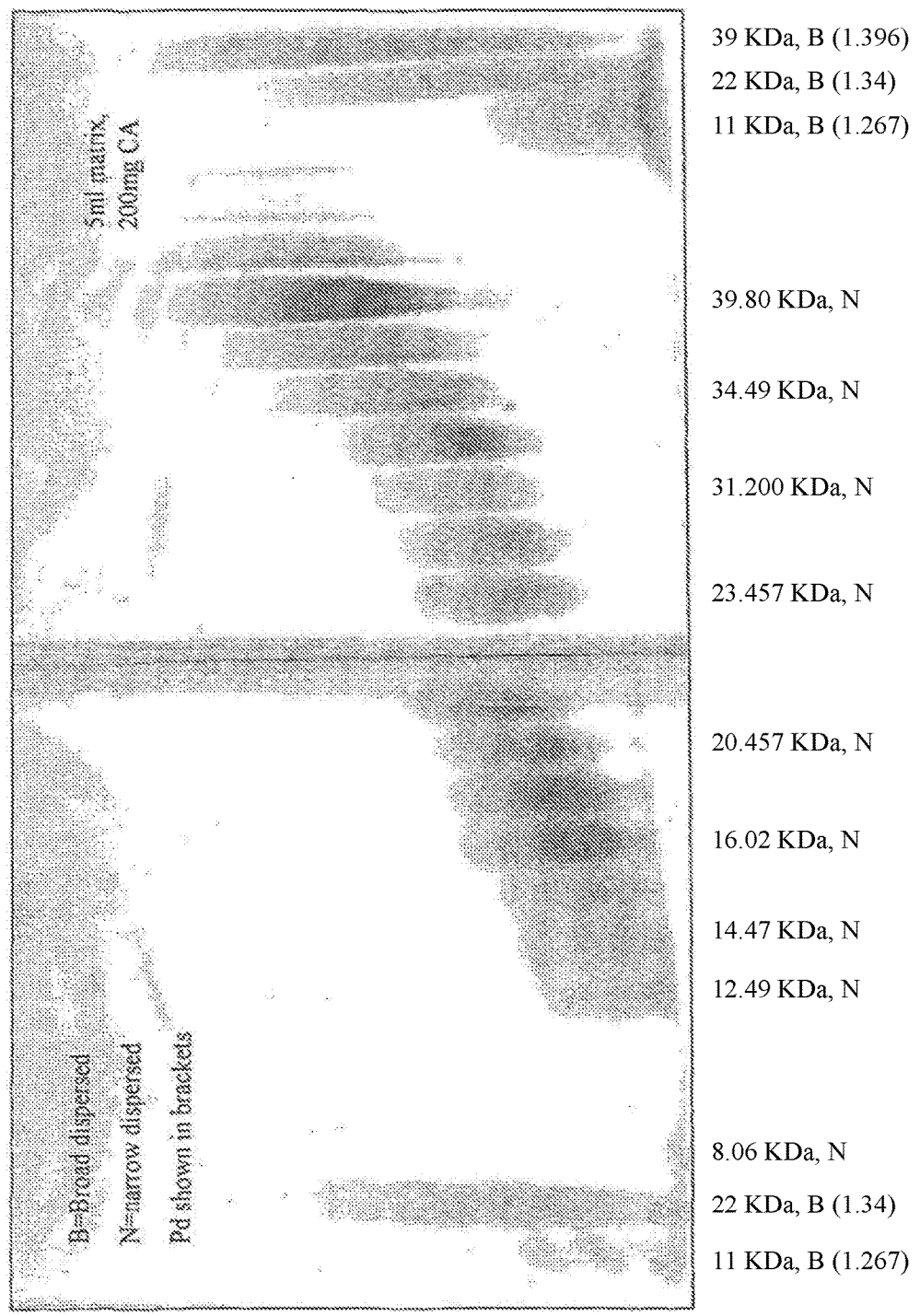
FIG. 5 shows a typical native page of CA with molecular weights.
Figure 6:
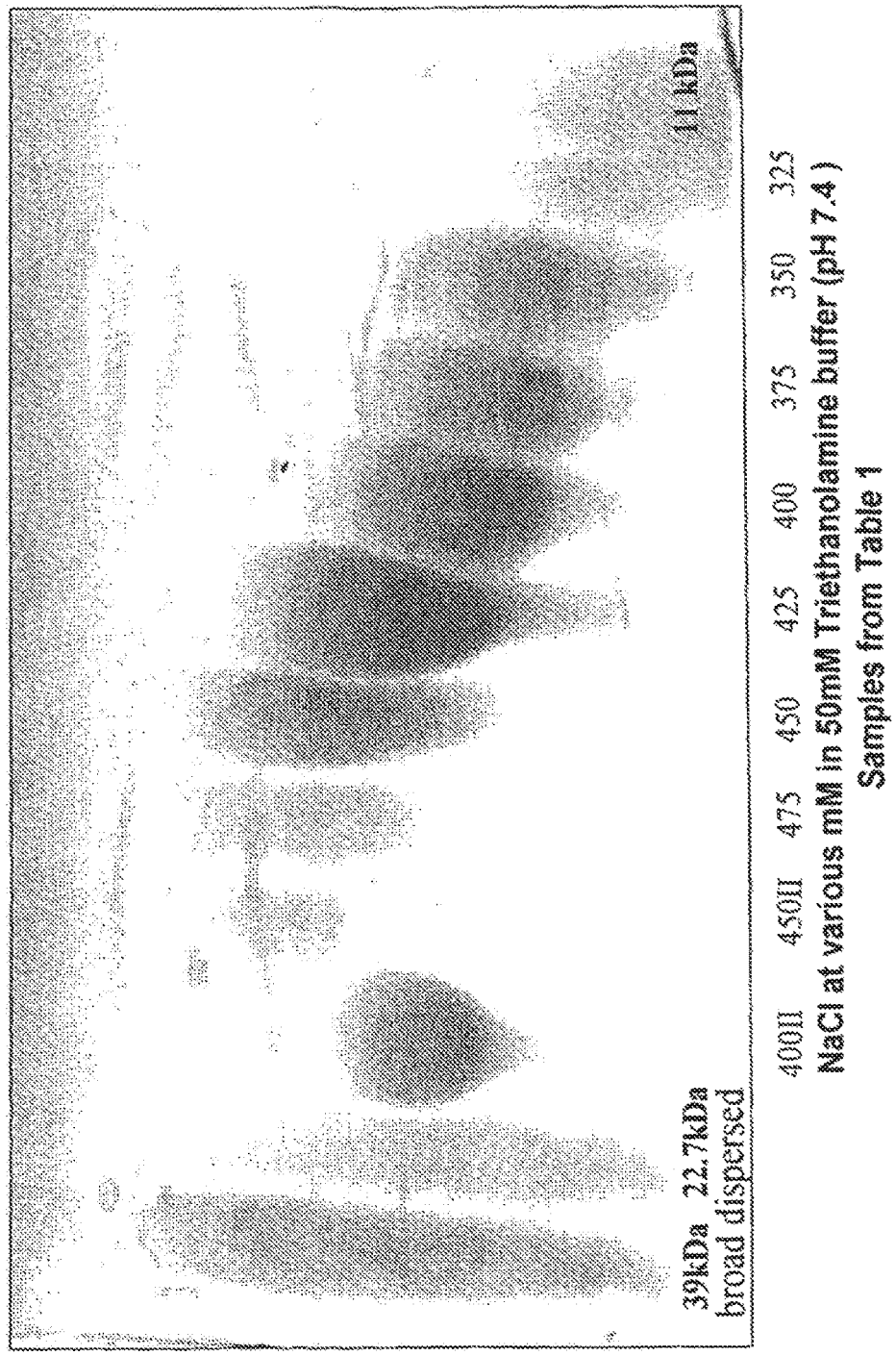
FIG. 6 shows the native PAGE of CA (22.7 KDa; pd 1.34)

CA and its derivatives (22.7 kDa) were successfully fractionated into 20 various narrow species with a polydispersity less than 1.1 with m.w. averages of up to 46 kDa with different % of populations (Tables 1-2 and FIGS. 4-8). Table 1 shows the results of fractionating the 22.7 kDa material at a scale of 75 ml. FIG. 7 is the GPC results and FIGS. 4-6 are native PAGEs of CA fractions.

TABLE 1

| IEC (22.7 KDa; 75 ml matrix; 3 g of CA) | | | |
|---|---|---|---|
| Elution buffers (in 20 mM Triethanolamine buffer + mM NaCl, pH 7.4) | M.W. | Pd | % Population |
| 325 mM | 12586 | 1.091 | 77.4% |
| 350 mM | 20884 | 1.037 | 3.2% |
| 375 mM | 25542 | 1.014 | 5.0% |
| 400 mM | 28408 | 1.024 | 4.4% |
| 425 mM | * | * | 7.4% |
| 450 mM | 43760 | 1.032 | 2.3% |
| 475 mM | 42921 | 1.096 | 0.2% |

* Not done

TABLE 2

Anion exchange chromatography of CA(22.7 KDa; pd 1.34):
Large Scale (900 matrix)

| Sample (in 20 mM Triethanolamine buffer + mM NaCl, pH 7.4) | M.W. | Pd |
|---|---|---|
| 350 mM | 15490 (1.008) | 10.470 (1.173) |
| 375 mM | 19960 (1.010) | 24659 (1.019) |
| 400 mM | 25829 (1.019) | 29573 (1.018) |
| 425 mM | 33763 (1.023) | 34160 (1.011) |
| 450 mM | 46880 (1.058) | 44400 (1.013) |
| 475 mM | — | 28500 (1.376) |
| 400 + 425 mM (mixed) | 26418 (1.082) | — |

This process was scalable from 1 ml to 900 ml of matrix with the fractionation profile almost identical at each scale (not all results shown).

Figure 8:
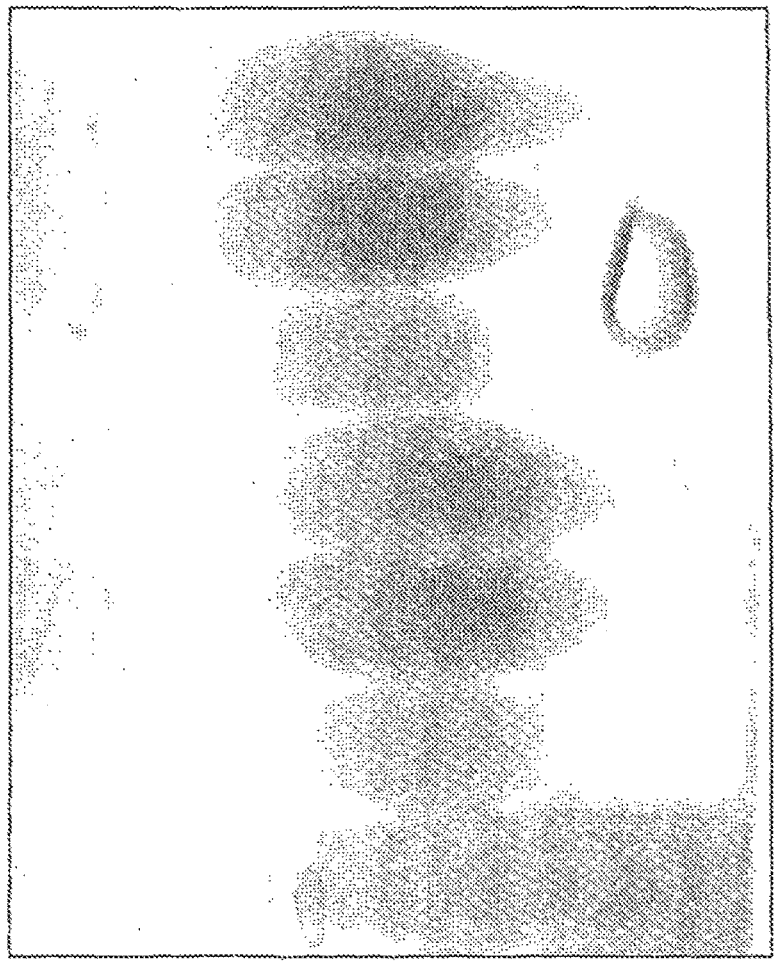
FIG. 8 shows the CA samples from different steps of fractionation.

The fractionation of larger polymer (CA, 39 kDa, pd 1.4) produced species up to 90 kDa. This process can successfully be used for the fractionation of even large batches of the polymer. FIG. 8 shows the native PAGE results for the 3 CA samples as supplied and for fractions separated by ion exchange analysed as in Table 3. The PAGE results show that the ion exchange fractions are narrowly dispersed. This is consistent with the GPC data shown in FIG. 7, which shows the results for 3 of the fractions separated from the 22.7 kDa CA (Table 3).

TABLE 3

| Sample | M.W. | Mn | PD |
|---|---|---|---|
| 1 | 18727 | 15016 | 1.25 (original CA) |
| 2 | 27677 | 25095 | 1.10 (fractionated CA) |
| 3 | 40950 | 40279 | 1.02 (fractionated CA) |

The 22.7 kDa material is separated on a larger scale. Using GPC the fractions from ion exchange are analysed.

All narrow fractions were successfully oxidised with 20 mM periodate and samples taken from different stages of the production process and analysed by GPC and native PAGE showed no change in the molecular weight and polydispersity. The data for some of the samples are shown in FIG. 8.

Example 3

Factors Affecting the Fractionation of CA

Figure 9:
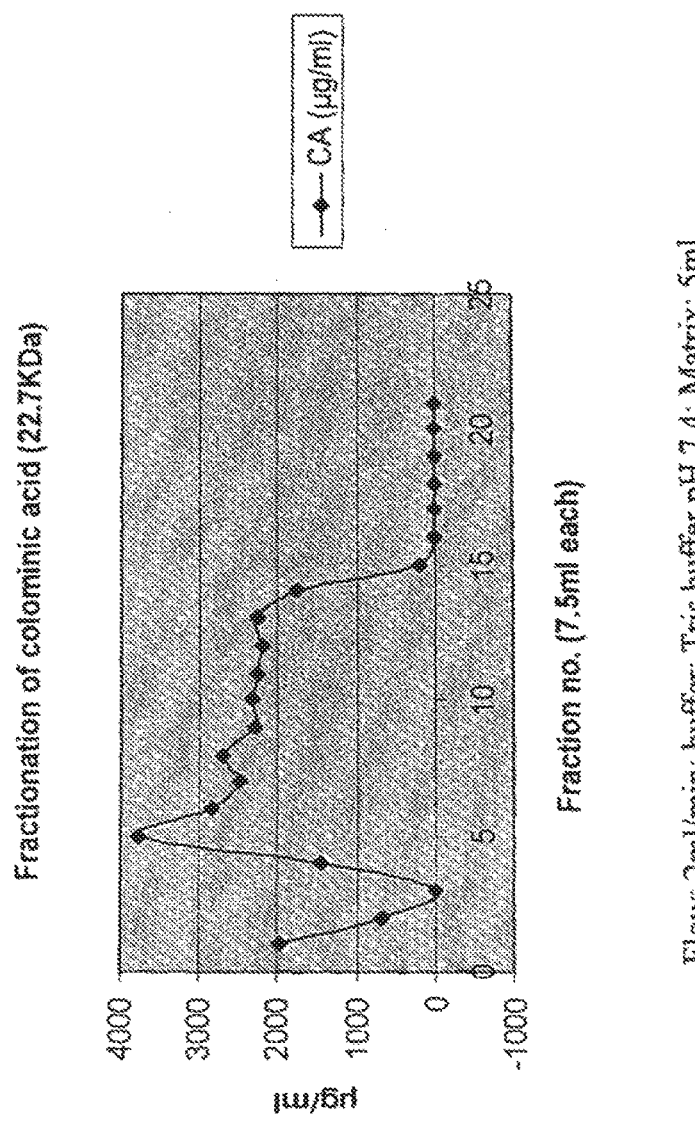
FIG. 9 shows the loading of different amounts of CA samples.
Figure 10:
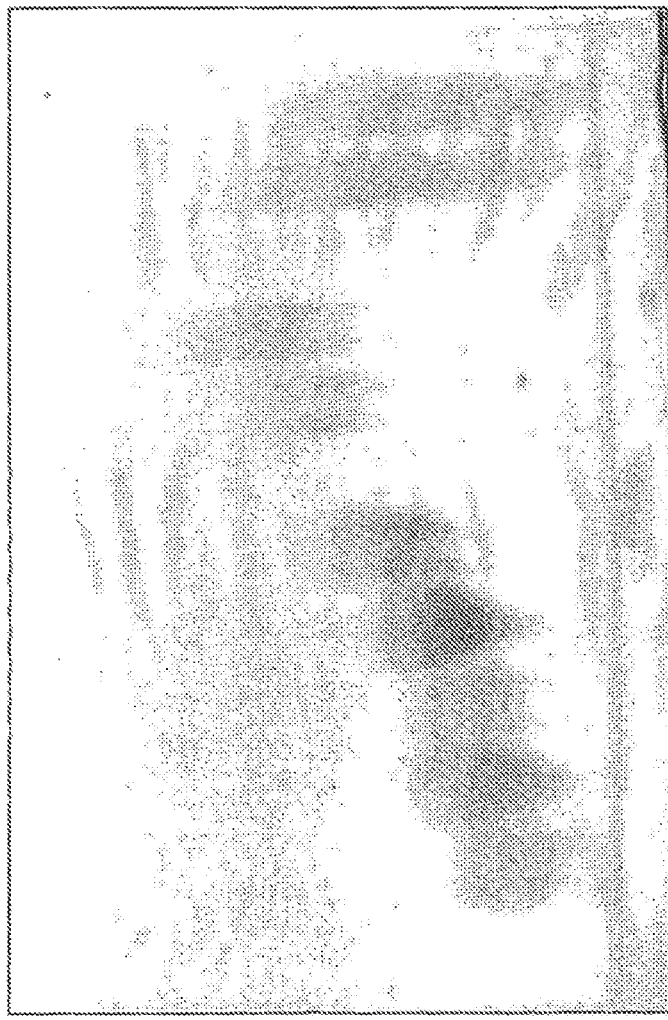
FIG. 10 shows the fractionation of CA (150 mg of CA; 5 ml matrix)
Figure 11:
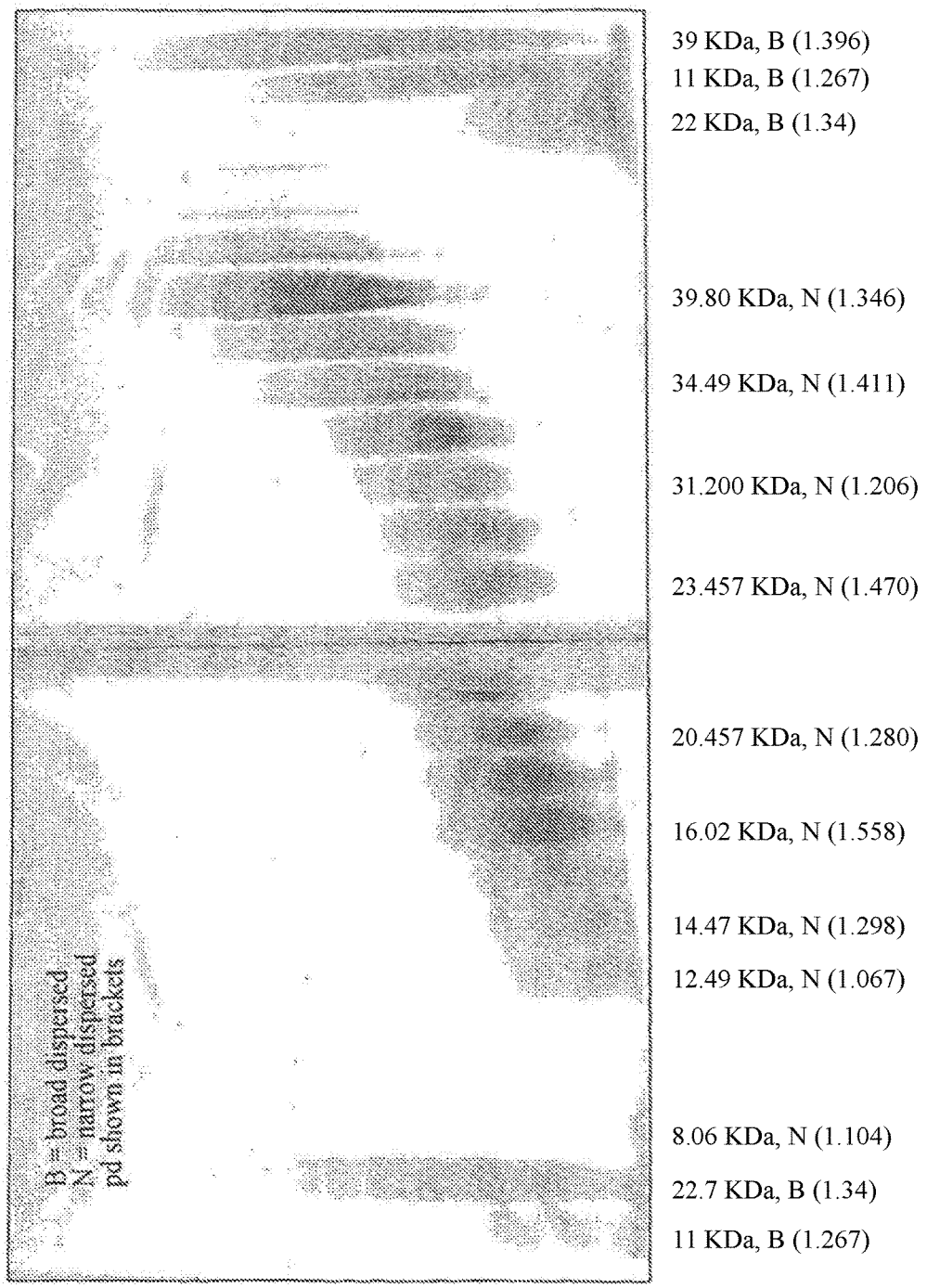
FIG. 11 shows the fractionation of CA (200 mg; 5 ml)

The various factors affecting the fractionation of CA (e.g. washing volume etc.) were studied [FIG. 7-14].
Results of Example 3: Factors Affecting the Fractionation of CA The various factors affecting the fractionation of CA were studied. The binding studies were done by loading 50, 100, 150 and 200 mg of CA on to the column (5 ml matrix). Using 200 mg of CA, more than 99% of CA was bound to the column (FIG. 9). When the column was washed with one column volume of eluting buffer, by step gradient, the polydispersity of polymer was found to be more than 1.1 (FIG. 11). The washing of the column with 1.5 column volume generated CA fractions with polydispersities less than 1.1 (FIG. 10).

Figure 12:
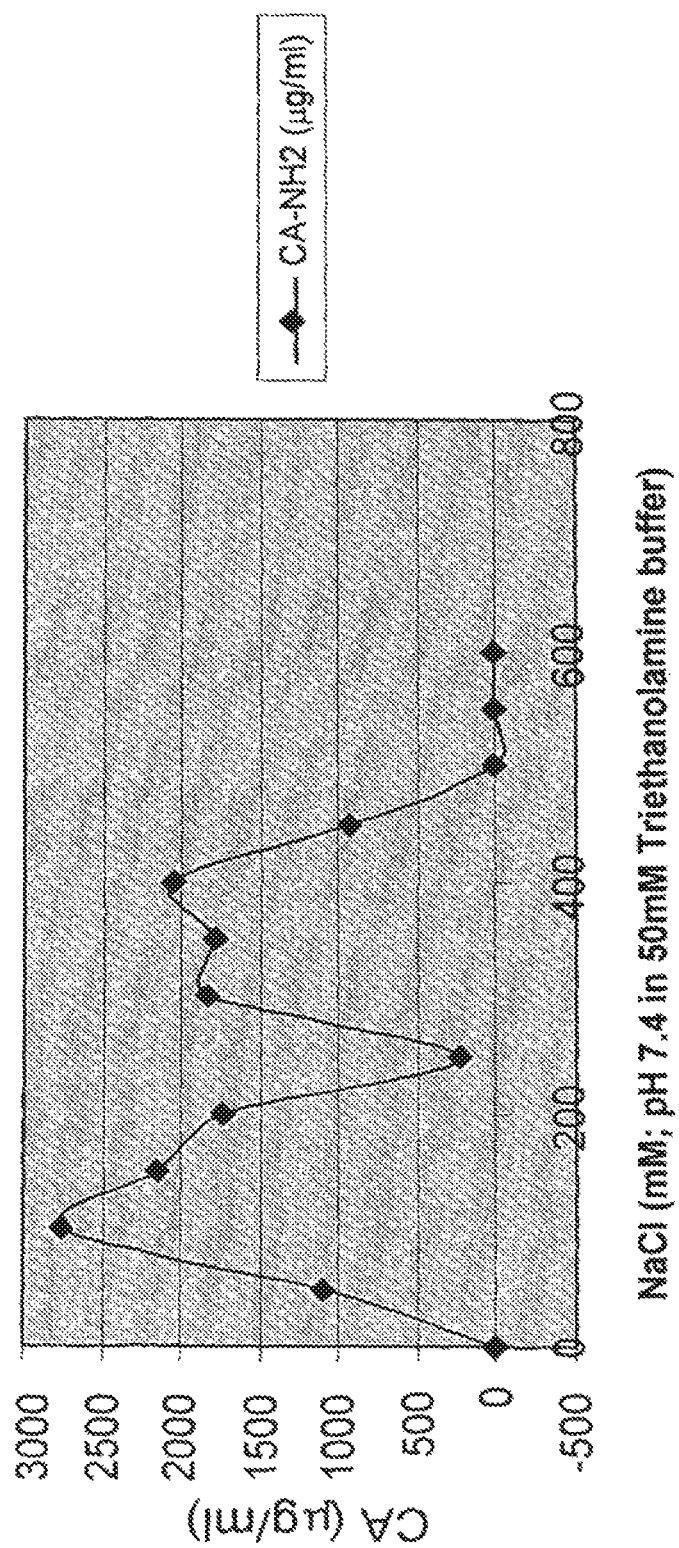
FIG. 12 shows the fractionation of CA-$NH_2$.
Figure 13:
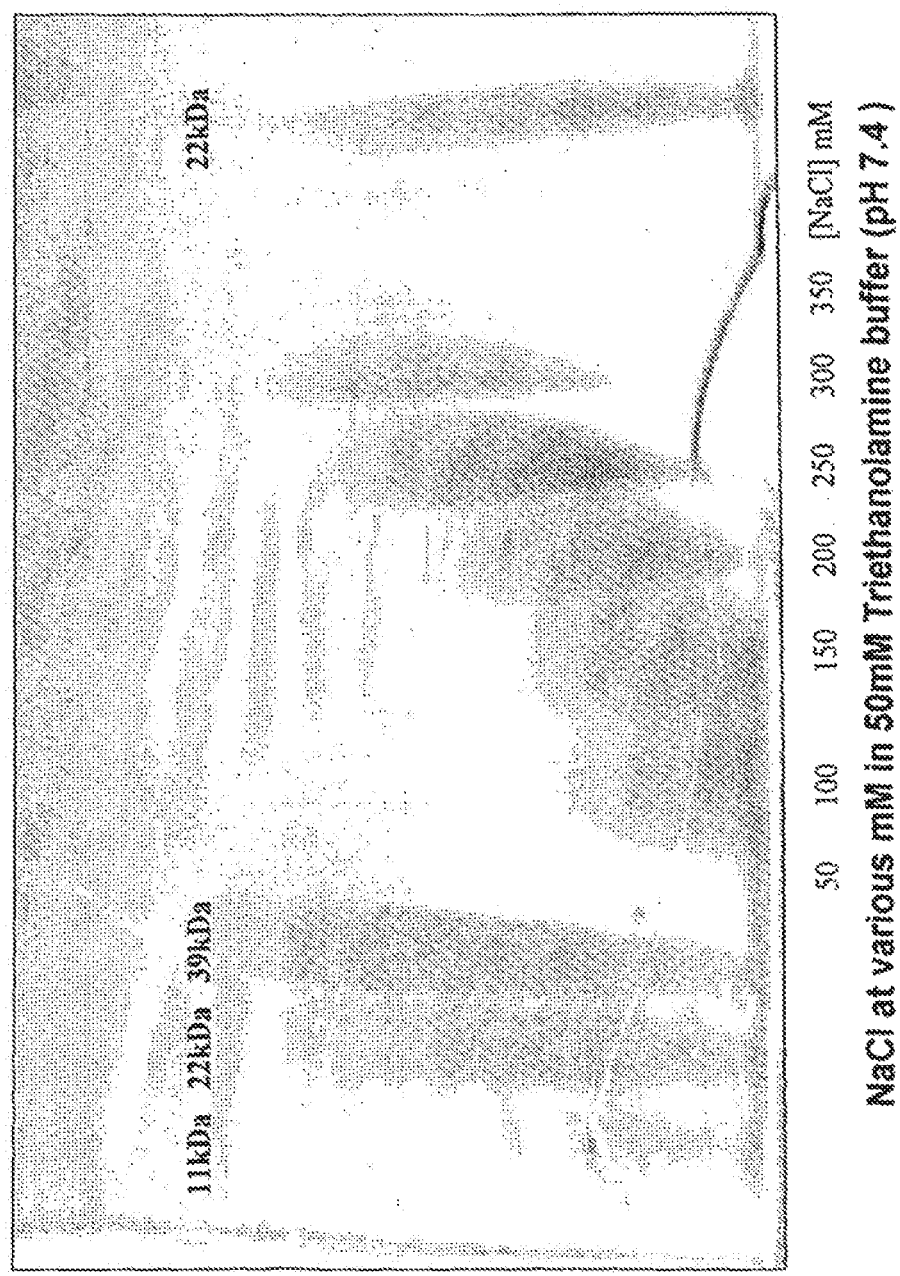
FIG. 13 shows the anion exchange chromatography of oxidised CA (22.7 KDa)
Figure 14:
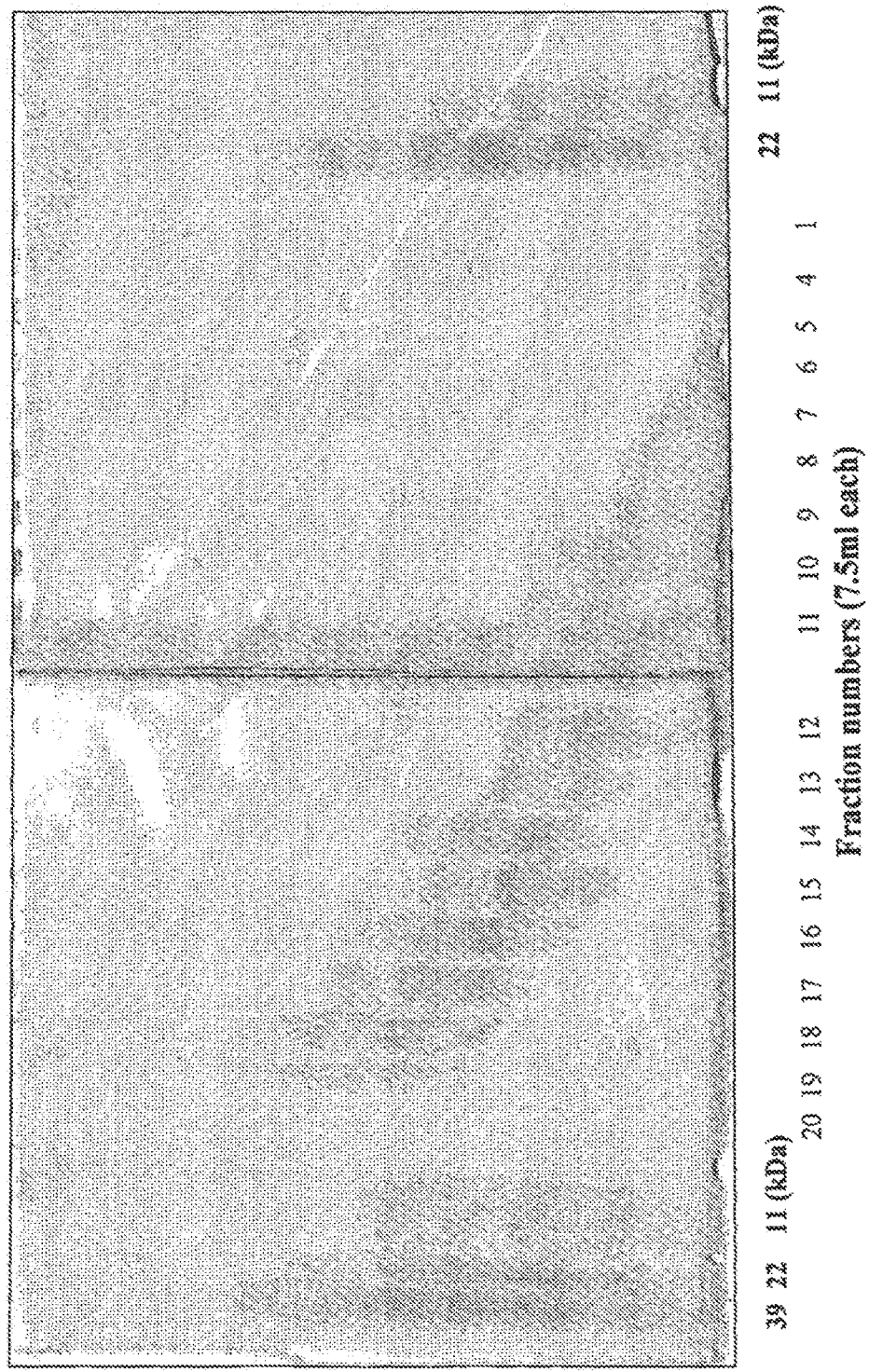
FIG. 14 shows the anion exchange chromatography of monofunctional CA.

The amino CA (CA-NH$_2$; FIG. 12), oxidised CA (FIG. 13) and monofunctional CA could successfully be fractionated in the fractions with polydispersity 1.1.

Example 4

Synthesis of Growth Hormone (GH) CA Conjugates (Broad and Narrow Dispersed)

Figure 15:
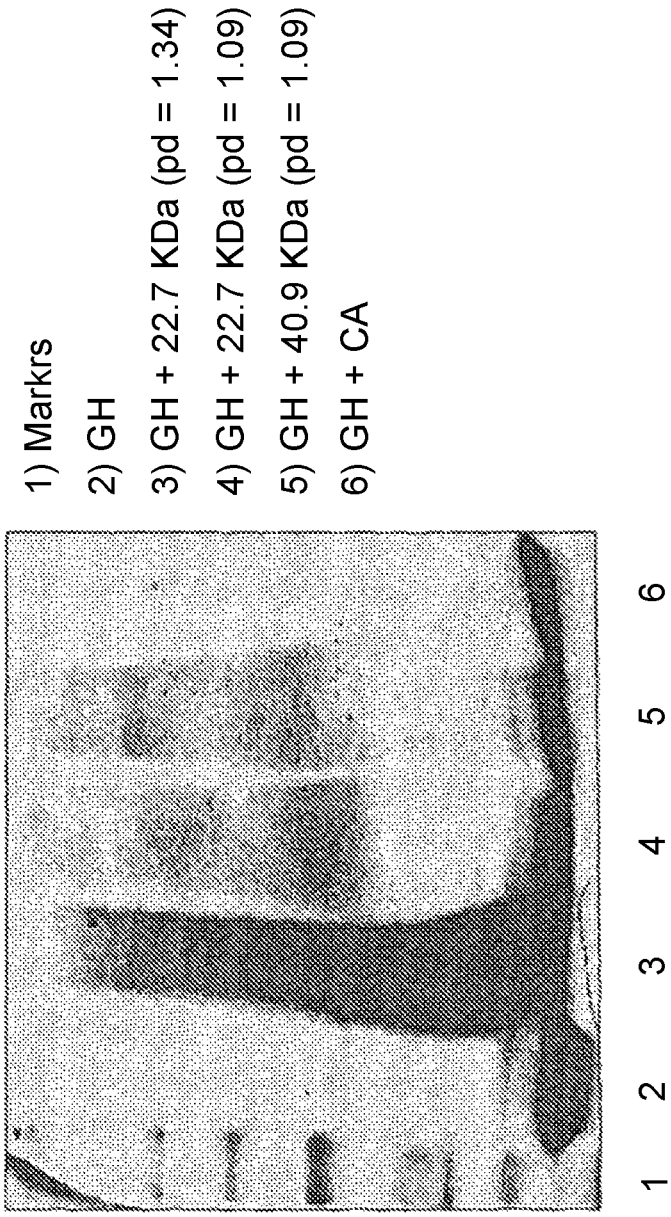
FIG. 15 shows SDS PAGE for preparation of protein-polymer conjugates with broad and narrow dispersed polymer.

CAO (22.7 KDa) and narrow dispersed-CAO (27.7 kDa pd=1.09; 40.9 kDa. pd=1.02) prepared in Reference example 2 were used for the preparation of GH conjugates.
Preparation of Growth Hormone—Ca Conjugates Growth hormone was dissolved in 0.15 M PBS (pH 7.4) and covalently linked to different CAs (CAO and NCAO). Different CAs (22 kDa, CAO; 27.7 kDa & 40.9 kDa, NCA) were individually added to GH (2 mg) in a CA:GH molar ratios (12.5:1), sodium cyanoborohydride was added to a final concentration of 4 mg/ml. The reaction mixtures were sealed and stirred magnetically for 24 h at 35±2° C. The mixtures were then subjected to ammonium sulphate ((NH$_4$)$_2$SO$_4$) precipitation by adding the salt slowly whilst continuously stirring, to achieve 70% w/v saturation, stirred for 1 h at 4° C., then spun (5000 xg) for 15 min and the pellets resuspended in a saturated solution of (NH4)2504 and spun again for 15 min (5000 xg). The precipitates recovered were redissolved in 1 ml PBS pH 7.4 and dialysed extensively (24 h) at 4° C. against the same buffer. Controls included subjecting the native protein to the conjugation procedure in the presence of non-oxidised CA or in the absence of CA. Shaking was kept to a minimum to avoid concomitant denaturation of the protein. Polysialylated GH was characterised by SDS-PAGE. The polysialylated GH was passed through anion exchange chromatography and the product fractions subjected to SDS PAGE (FIG. 15).
Results of example 4: Synthesis of GH-CA Conjugates (Broad and Narrow Dispersed)

Figure 19:
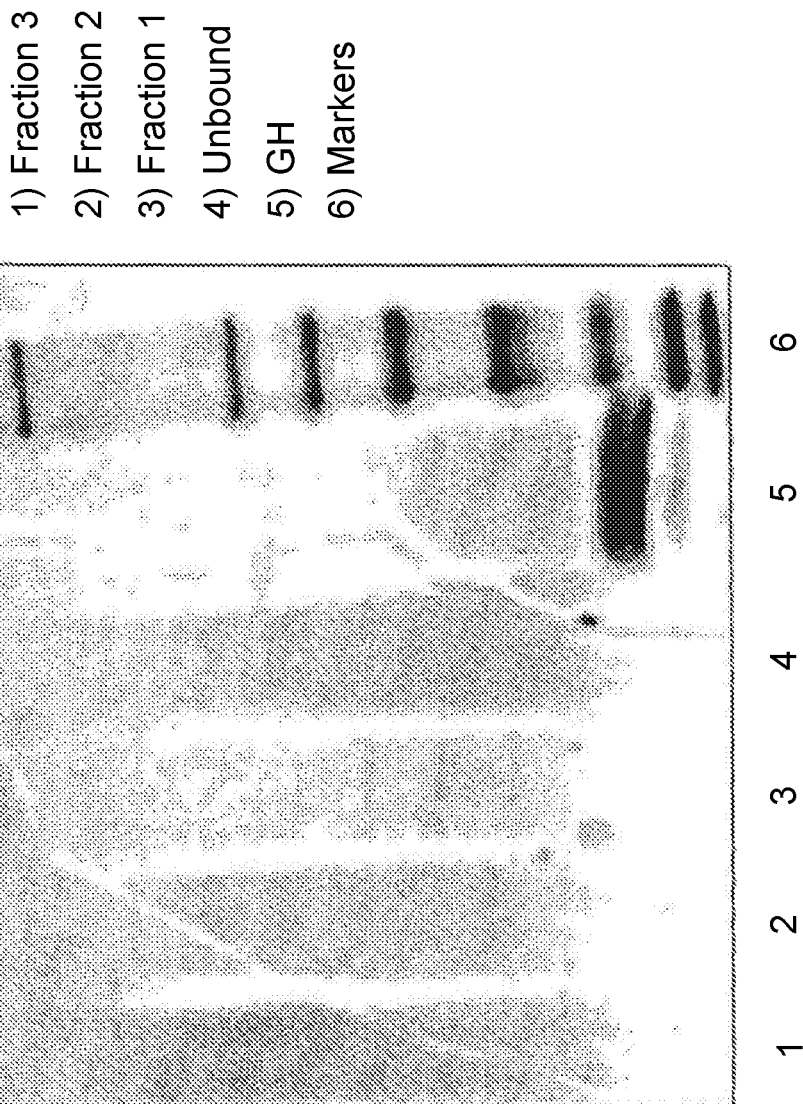
FIG. 19 shows the anion exchange chromatography of GH-CA conjugates.

The GH-CA conjugates were successfully synthesised. The results of SDS-PAGE (FIG. 15) show that in the control (with GH) migration of the sample is similar to that for fresh GH. In the conjugate lanes there are shifts in the bands which typically indicates an increase in mass indicative of a polysialylated-GH. The band width was significantly narrowed down in case of conjugates with narrow dispersed polymer in comparison to conjugates with broad dispersed polymers. Further, GH conjugates (with broad dispersed polymer) were successfully separated into different species by anion exchange chromatography (FIG. 19).

Example 5

Precipitation of CA

Figure 16:
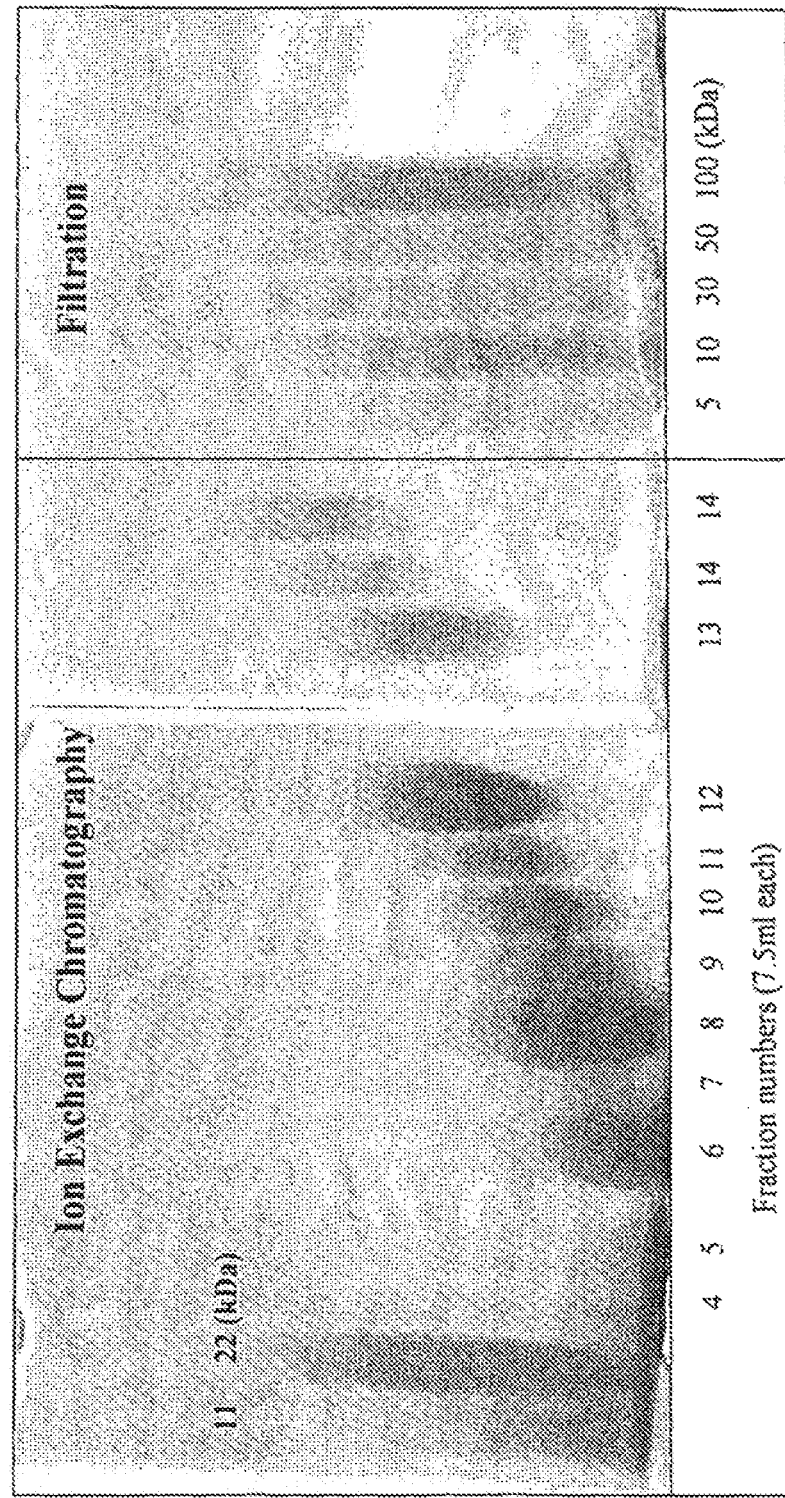
FIG. 16 shows native PAGE results for fractionation of CA by anion exchange chromatography vs filteration.
Figure 17:
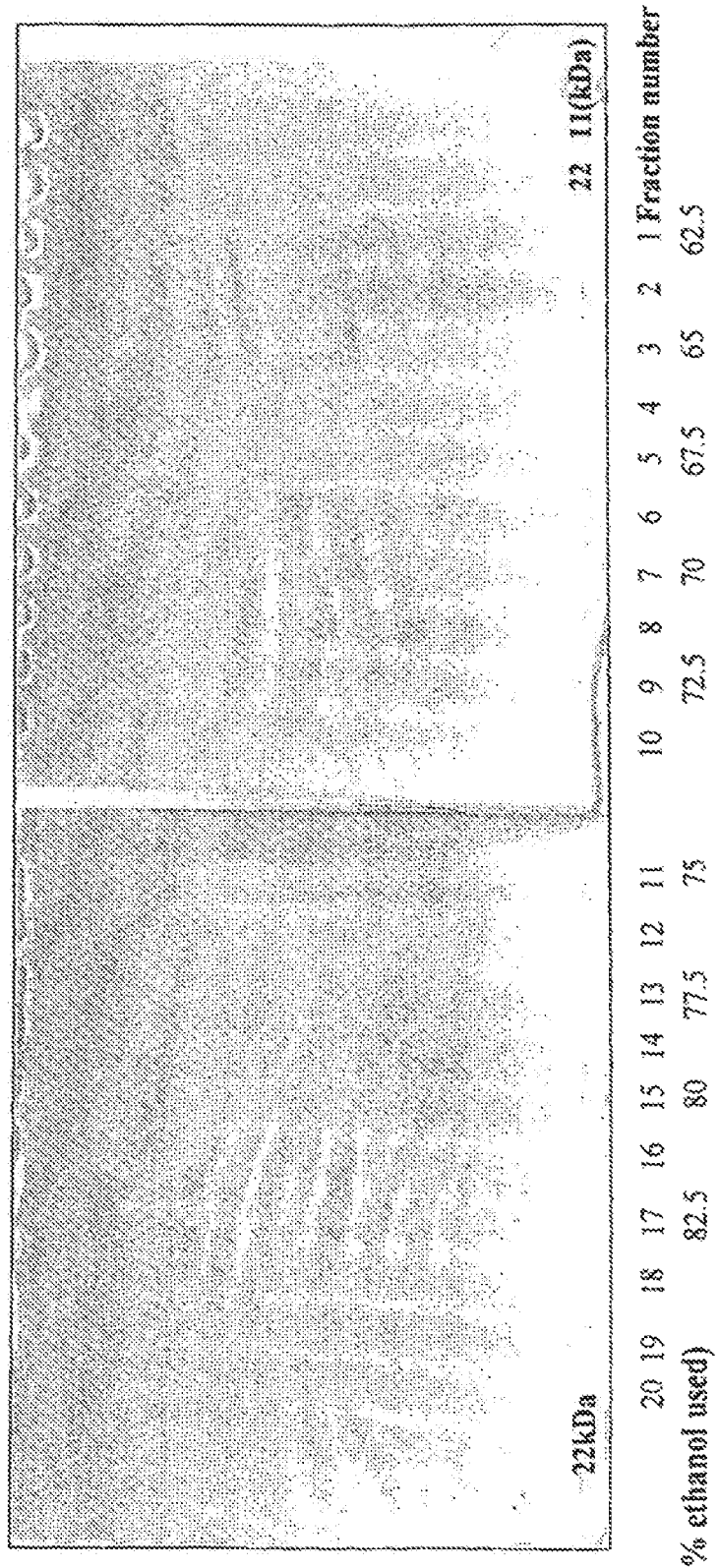
FIG. 17 shows the fractionation of CA by ethanol precipitation.

Differential ethanol precipitation was used to precipitate different chain lengths of colominic acid [FIG. 16, 17].
Results of Example 5: Precipitation of CA The CA (22.7; pd 1.34) could not be precipitated into narrow dispersed fractions using different strengths of ethanol (FIG. 17). However, differential ethanol precipitation showed that smaller narrow CAs required more ethanol (EtOH). Broad 22.7 kDa polymer was precipitated with 70% EtOH giving a yield >80% of product polymer. A concentration of 80% EtOH was required to precipitate >80% of a lower MW 6.5 KDa (pd<1.1). This process also removes part of the salt contaminating the product.

Example 6

Fractionation of CA by Ultrafiltration

Samples of 22.7 kDa were purified by ultrafiltration over different molecular weight cut off membranes (5, 10, 30, 50, and 100 kDa). In all cases retentate was examined by GPC and native PAGE [FIG. 18].

Results of Example 6: Fractionation of CA by Ultrafiltration

Figure 18:
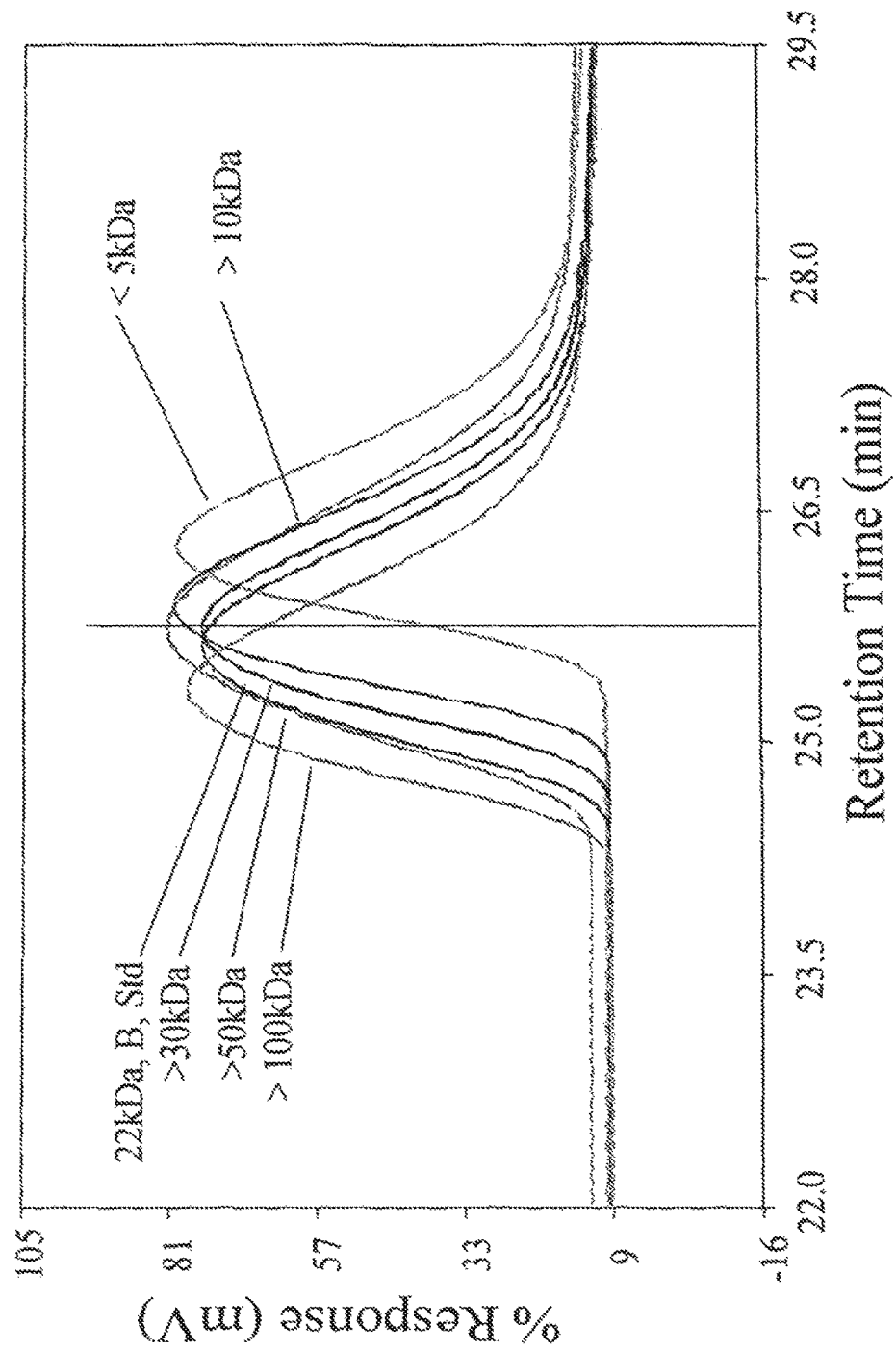
FIG. 18 shows the fractionation of CA by ultrafilteration.

Samples of 22.7 kDa purified by ultrafiltration over different molecular weight cut off membranes showed that there was a decrease in polydispersity of the polymer and a shift towards higher molecular weight with increase in membrane cut off (FIG. 18). FIG. 16 shows fractionation of CA by anion exchange chromatography (left) and filtration (right). IEC of CA generated fractions with much narrow dispersed CAs as compared to fractionation by filtration.

Example 7

Characterization by NMR Spectroscopy

Figure 20:
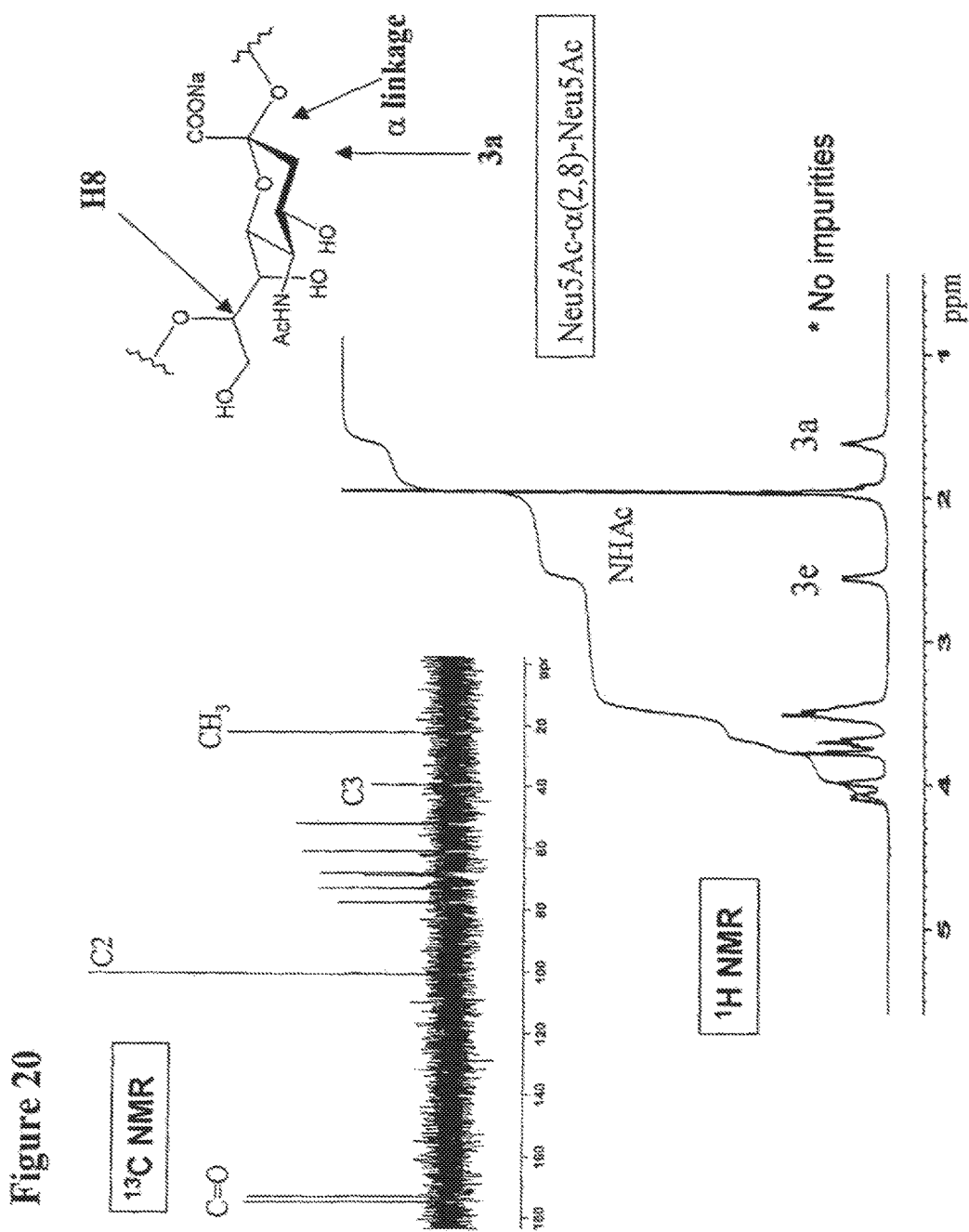
FIG. 20 shows the characterization of CA (35 KDa) by NMR.

The fractionated CA polymers were characterized by $^1$H (400 MHz) and $^{13}$C (100 MHz) NMR spectroscopy for impurities (if any) using $D_2O$ (FIG. 20).
Results of Example 7: Characterization by NMR Spectroscopy The $^1$H and $^{13}$C NMR of narrow dispersed polymer fractionated material is free from impurities. In addition, the chemical shifts of the H-3 protons in the $^1$H NMR and the C-2 carbon in the $^{13}$C NMR spectra confirm that the polymer is indeed the expected alpha-2,8 linked sialic acid material.

Example 8

Fractionation of CA (39 kDa, pd 1.4) by IEC 8.1 Fractionation at Large Scale

An XK50 column (Amersham Biosciences, UK) was packed with 900 ml Sepharose Q FF and equilibrated with 3 column volumes of wash buffer (20 mM triethanolamine; pH 7.4) at a flow rate of 50 ml/min. CA (12.5 g in 200 ml wash buffer) was loaded on column at 50 ml per minute via a syringe port. This was followed by washing the column with 1.5 column volumes (1350 ml) of washing buffer.

The bound CA was eluted with 1.5 column volumes of elution buffer (triethanolamine, 20 mM, pH 7.4) containing different salt concentrations (0, 200, 250, 300, 350, 375, 400, 425, 450, 475, 500 and 525 mM NaC) and finally with 1000 mM NaCl in the same buffer to remove all residual CA and other residues (if any).

The samples were concentrated to approximately 20 ml by either high-pressure ultrafiltration over a 3 or 10 kDa membrane (Vivascience, UK) or by Vivaflow 50 diafiltration (filtration by constantly passing the sample through a membrane) having a 3 kDa mwco membrane (Vivascience, UK). These samples were buffer exchanged into deionised water by either repeated ultrafiltration or Vivaflow at 4° C. The samples were analysed for average molecular weight and other parameters by GPC (as reported in Example 2) and native PAGE (4-20% Tris-glycine gel stained with alcian blue) (FIGS. 21 and 22).
8.2 Fractionation at Small Scale CA was also fractionated on a smaller scale (200 mg of CA) using Sepharose Q FF (5 ml matrix, prepacked; Amersham Biosciences, UK) employing an identical buffer system (20 mM triethanolamine; pH 7.4) containing different salt concentrations (0, 200, 250, 300, 350, 375, 400, 425, 450, 475, 500, 525, 550 and 575 mM NaCl). The bound CA was eluted by washing the column with 1.5 column volumes (7.5 ml) at a flow rate of 1 ml/min with a final wash of the column using 1000 mM NaCl in the usual triethanolamine buffer.

The samples were concentrated to approximately 0.75 ml by Vivaspin membrane filtration (mwco 3 kDa) (Vivascience, UK), buffer exchanged into deionised water by repeated membrane filtration at 8° C. and then lyophilised.

Figure 22:
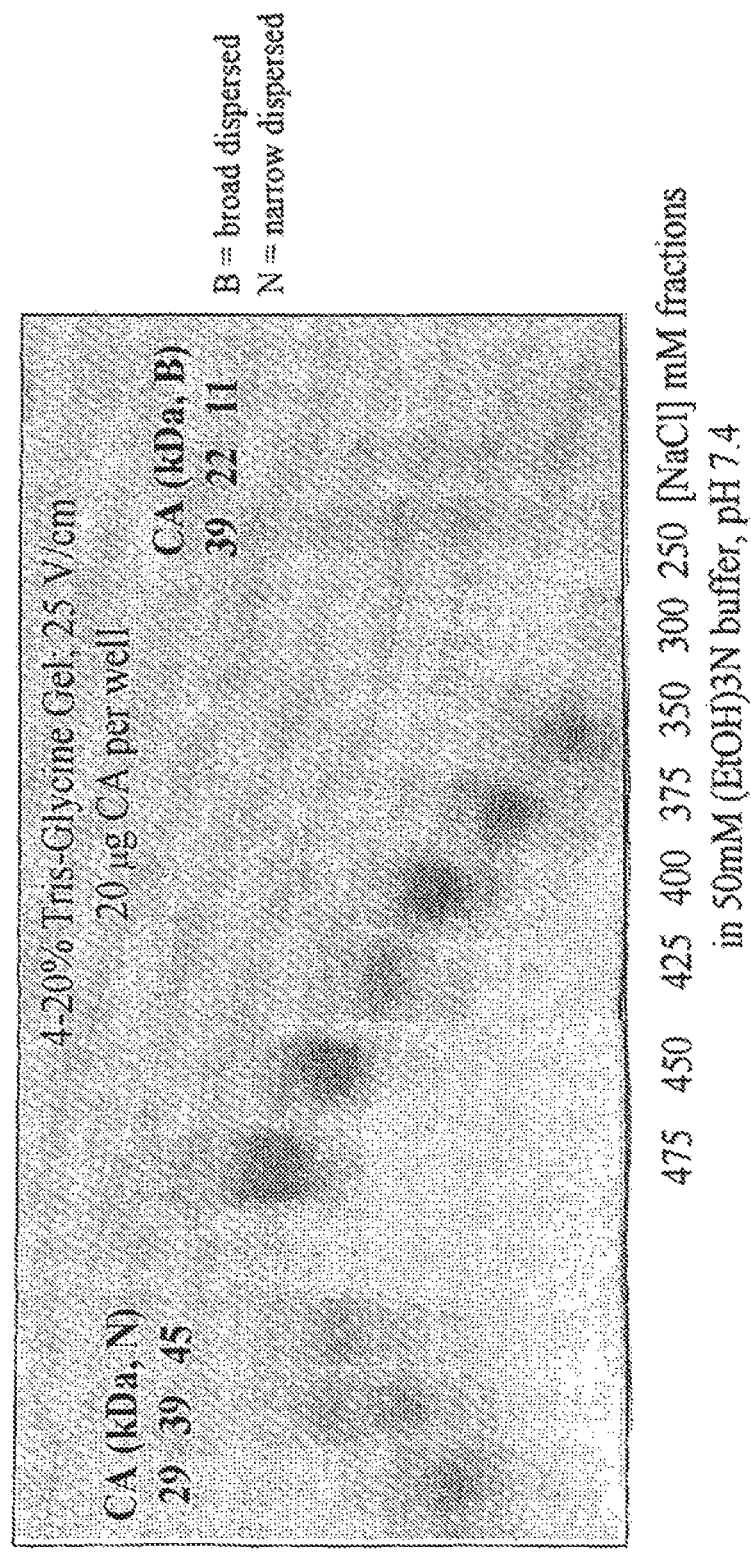
FIG. 22 shows the native PAGE of CA (39 kDa; 12.5 g) IEC fractions.
Figure 23:
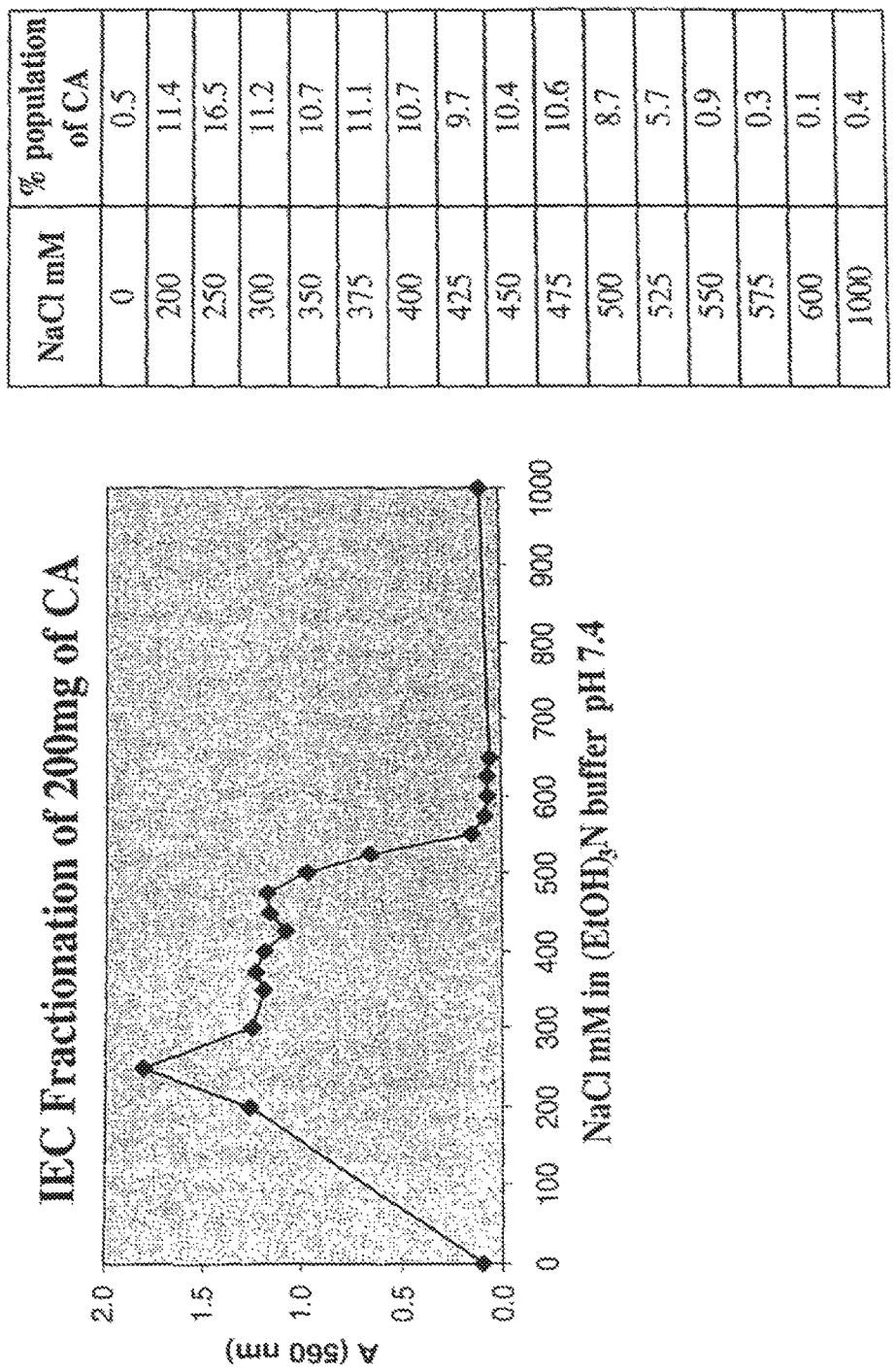
FIG. 23 shows % population of small scale IEC fractionation of CA (39 kDa; pd 1.4)
Figure 24:
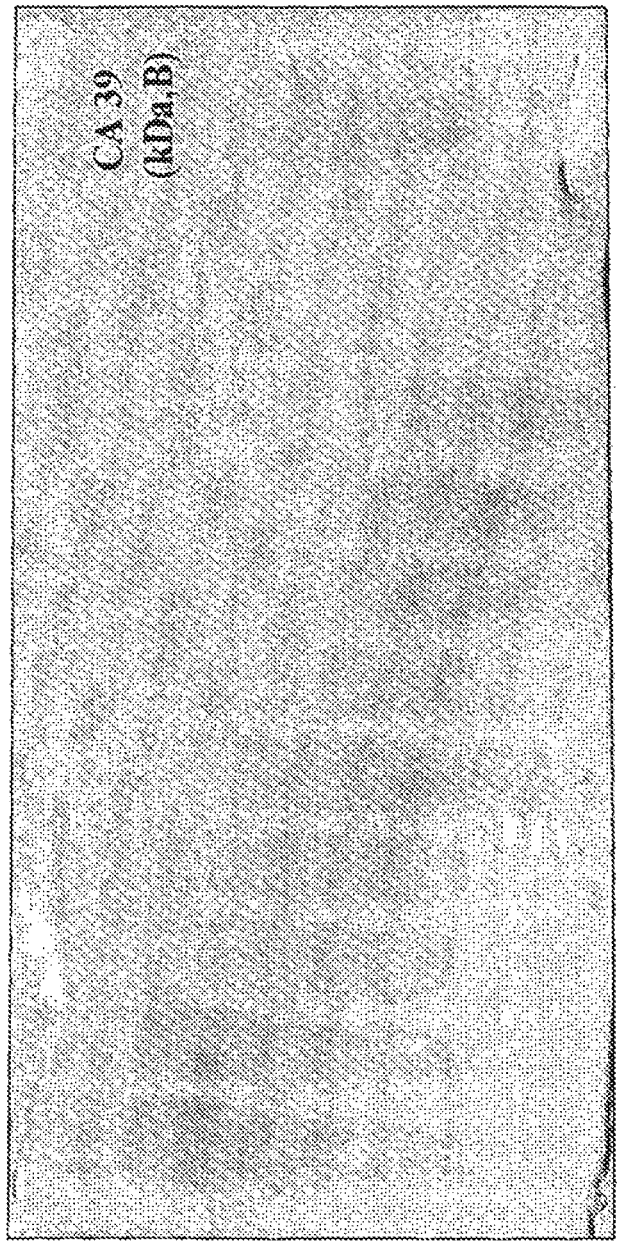
FIG. 24 shows the native PAGE of CA (39 kDa; 200 mg) IEC fractions.

The samples were analysed by native PAGE (4-20% tris-glycine gel stained with alcian blue) (FIGS. 23 and 24).
Results of Example 8: Polydispersed CA (39 kDa; pd 1.4) was successfully fractionated into various narrow dispersed species with molecular weight averages ranging from 7 to 97 kDa and with different % of populations (FIGS. 21-24 and Table 4).

TABLE 4

GPC analysis of various fractionated CA

| CA fraction | Mw (kDa) | pd |
|---|---|---|
| 475 | 97.2 | 1.285 |
| 450 | 52.3 | 1.109 |
| 425 | 37.9 | 1.062 |
| 400 | 28.0 | 1.048 |
| 375 | 19.0 | 1.080 |
| 350* | 14.5 | — |
| 300* | 10.0 | — |
| 250* | 7.0 | — |

*Estimated approximate values by native PAGE

In the analysis the solvent used was 0.2M $NaNO_3$ in MECN and PEO and dextron were used as standards. The temperature was 22° C., 3 injection volume 100 pL and flow rate was 0.7 mL/mn.

Figure 21:
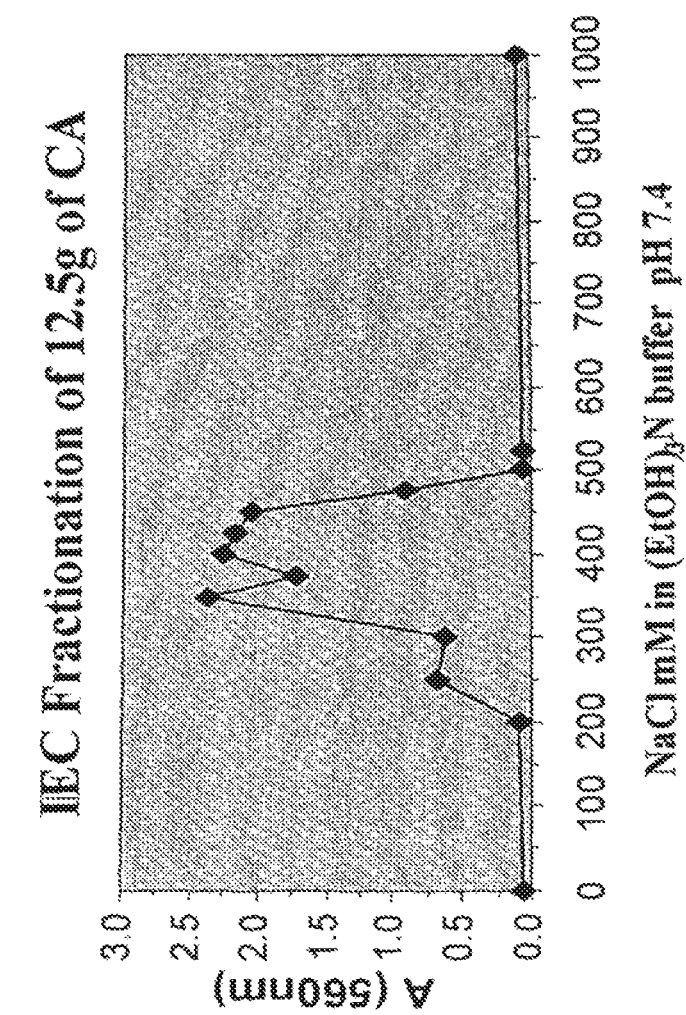
FIG. 21 shows % population of large scale IEC fractionation of CA (39 kDa; pd 1:4)

FIGS. 21 and 23 show the % population of CA in various fractions as a result of fractionating 39 kDa CA polymer on a large scale (12.5 g CA; 900 ml matrix) and a small scale (200 mg CA; 5 ml matrix), respectively. FIGS. 22 and 24 are the native PAGEs obtained as a result of the fractionation of CA on a large and small scale. Table 4 is the GPC results of the fractions obtained by IEC at various salt concentrations. The GPC data shows that species up to 97 kDa are generated by the fractionation process (see Example 9 for further details). These larger molecular weight polymers have been shown to have a greater percentage phosphate moiety present on the reducing end of CA compared to their lower molecular weight counterparts by a phosphate assay, which tests for the presence of inorganic phosphate (Rouser et. al. 1970).

Example 9

Characterisation of Fractionated CA by GPC

Freshly prepared CA samples, by dissolving for example either CA, CAO, CAOR or CAORO (4-5 mg/ml) in 0.2 M $NaNO_3$/0.1% $NaN_3$/10% acetonitrile (1 ml) (or alternatively 10 mM PBS, pH 7.4) and then filtering the resulting solution over 0.2 μm nylon membrane (Whattman, UK), were analysed by GPC.

Samples were chromatographed with 2× GMPWxl (250× 4.6 mm) columns employing a triple detection GPC (SEC$^3$) system (Viscotek Europe Ltd, UK). Detectors consisted of a Viscotek Laser Refractometer (refractive index) and a Viscotek 270 Dual Detector (right-angle light scattering detector configured with a 4-capillary viscometer detector) collated with an OmniSEC 3.1 workstation (Viscotek Europe Ltd).

The analysis conditions used were; eluent: buffer employed to dissolve the CA sample; flow rate: 0.7 ml/min; sample loading: 100 μl; temperature: 22° C. The system was calibrated with narrow molecular weight polyethylene glycol and broad molecular weight Dextran reference materials.

The time it takes for a polymer to be eluted from the GPC column is converted to its molecular weight using various detectors. The light scattering detector provides a direct measurement of absolute molecular weight and eliminates the need for column calibration (detector gives a proportional response to molecular weight and concentration). The radius of gyration is not calculated when measurements are performed using a single angle. The viscometer provides a direct measurement of intrinsic viscosity and allows for the determination of molecular size, conformation and structure (detector gives an inversely proportional response to molecular density). The response from the refractive index detector is proportional to the concentration of polymer: the constant of proportionality is dn/dc (the same specific refractive index increment needed in light scattering).

The GPC system described above enables a number of parameters of CA to be determined. For instance, the number average molecular weight (Mn) and the weight average molecular weight (Mw) can be obtained and from these numbers the polydispersity of CA can be calculated. Other information acquired from the GPC data include the percentage recovery of CA and the degree of branching (if any) on the polymer. The exact concentration of the sample can also be determined from the dn/dc value (or alternatively the dn/dc value can be calculated from the exact known concentration of the polymer).

Results of Example 9: Table 5 shows typical data for a range of parameters that was obtained from the analysis of a CA fraction (400 mM NaCl in 20 mM triethanolamine, pH 7.4) from IEC fractionation of CA (39 kDa, pd 1.4). In this table, the following definitions apply:

Mn=number average molecular weight
Mw=weight average molecular weight
Mz=Z-average molecular weight
Mp=peak average molecular weight
My=viscosity average molecular weight
Mw/Mn=molecular weight distribution (polydispersity)
Rh=hydrodynamic radius
IV=intrinsic viscosity
dn/dc=change in refractive index with concentration for the sample

TABLE 5

Typical GPC data of the CA fraction (400 mM NaCl in 20 mM triethanolamine, pH 7.4) from IEC

| Parameters | Values |
| --- | --- |
| Mn (Da) | 26,666 |
| Mw (Da) | 27,956 |
| Mz (Da) | 31,129 |
| Mp (Da) | 22,969 |
| Mw/Mn | 1.048 |
| IV (dl/g) | 0.2395 |
| Rh (nm) | 4.683 |
| Branches | 0.00 |
| Sample Conc (mg/ml) | 5.600 |
| Sample Recovery (%) | 90.71 |
| dn/dc (ml/g) | 0.156 |
| dA/dc (ml/g) | 0.000 |
| Mark-Houwink a | −0.048 |
| Mark-Houwink logK | −0.425 |

Figure 25:
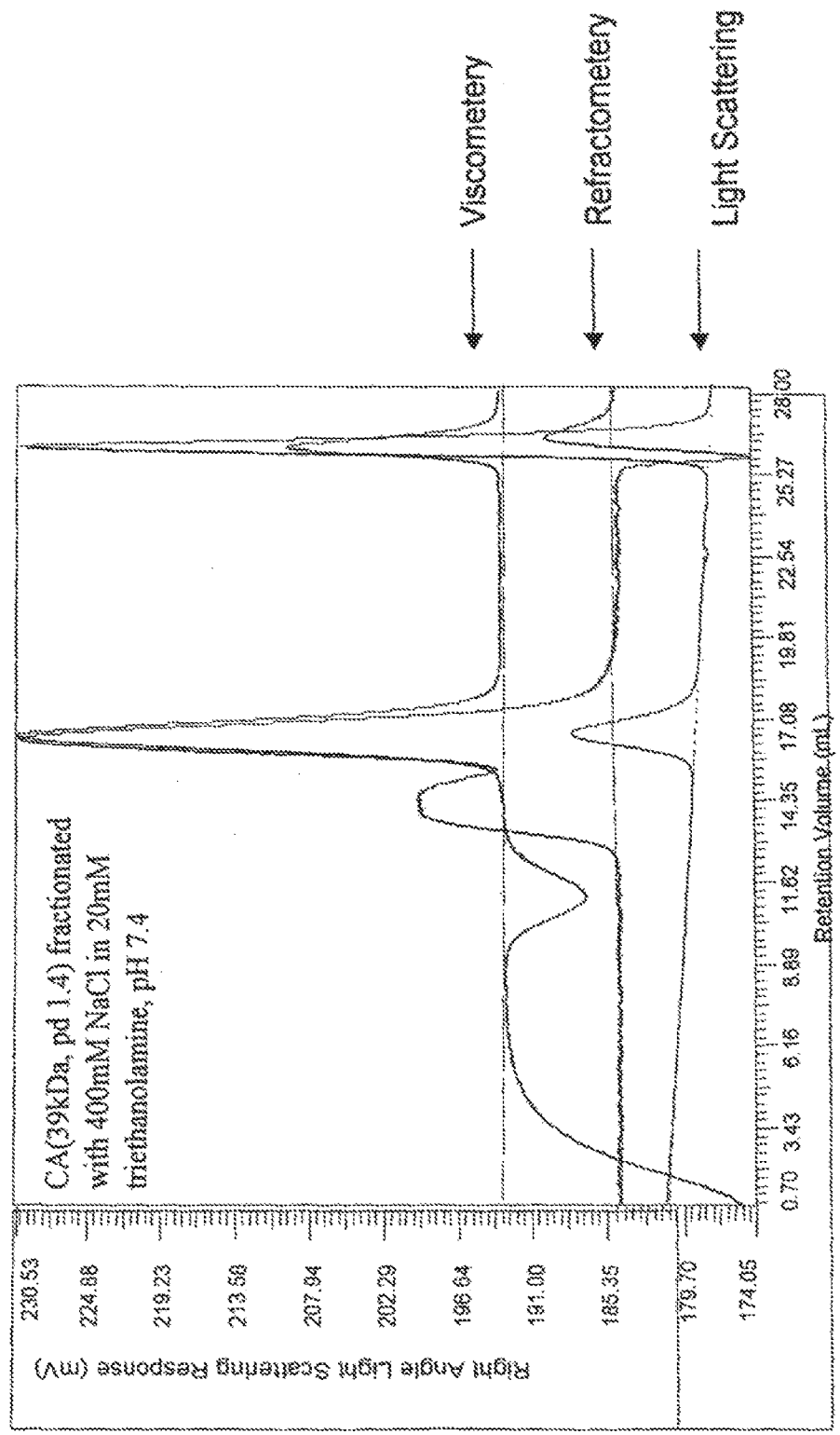
FIG. 25 shows a typical GPC chromatogram for a narrow dispersed CA.

For example, 27,956 and 26,666 Da were the values for Mw and Mn, respectively, which gave a polydispersity of 1.048. Table 4 shows the range of narrow dispersed molecular weights obtained by GPC analysis on the fractionation of polydispersed CA (39 kDa; pd 1.4) with IEC, while FIG. 25 shows a typical GPC chromatogram for the combined viscometer, refratometer and light scattering curves obtained for a narrow dispersed CA sample.

Example 10

Optimisation Studies 10.1 Optimisation of the Analysis of CA by Native PAGE

Fractionated and the non-fractionated CA have been analysed further by TBE and Tris-glycine gels on native PAGE in order to optimise the resolution of these polymers on the gel. In general, 40 ig of either narrow or broad dispersed CA was loaded, as a 20 il solution containing 10 il of loading buffer, per well on the gel. The gel was run at three different speeds (150, 25 or 15 mV/cm) and then stained with alican blue, followed by destaining with 2% acetic acid.

Figure 26:
FIG. 26 shows optimisation of native-PAGE analysis of CA.

Results of Example 10.1: FIG. 26 demonstrates the various resolutions that can be obtained for different molecular weights of CA with 4-20% Tris-glycine, 4-20% and 20% TBE gels. From the gels it can be observed that good separation of high and low molecular weight CAs can be observed with 4-20 and 20% TBE gels, with particularly good resolution with the 20% TBE gel. Narrow bands are best observed when the gel is run at 25 or 15 mV/cm compared to when the gel speed is 150 mV/cm.

10.2 Concentration of CA

Figure 27:
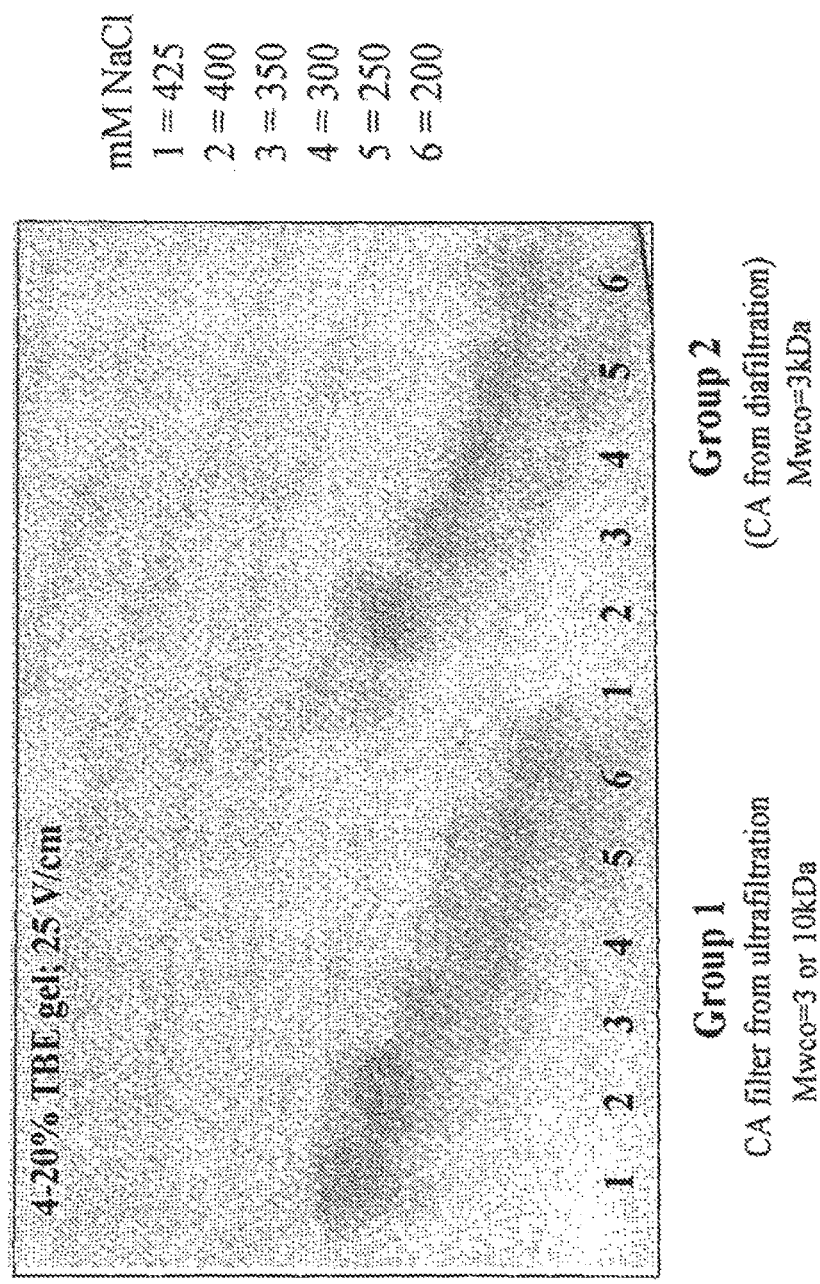
FIG. 27 shows native PAGE of CA fractions from IEC.
Figure 28:
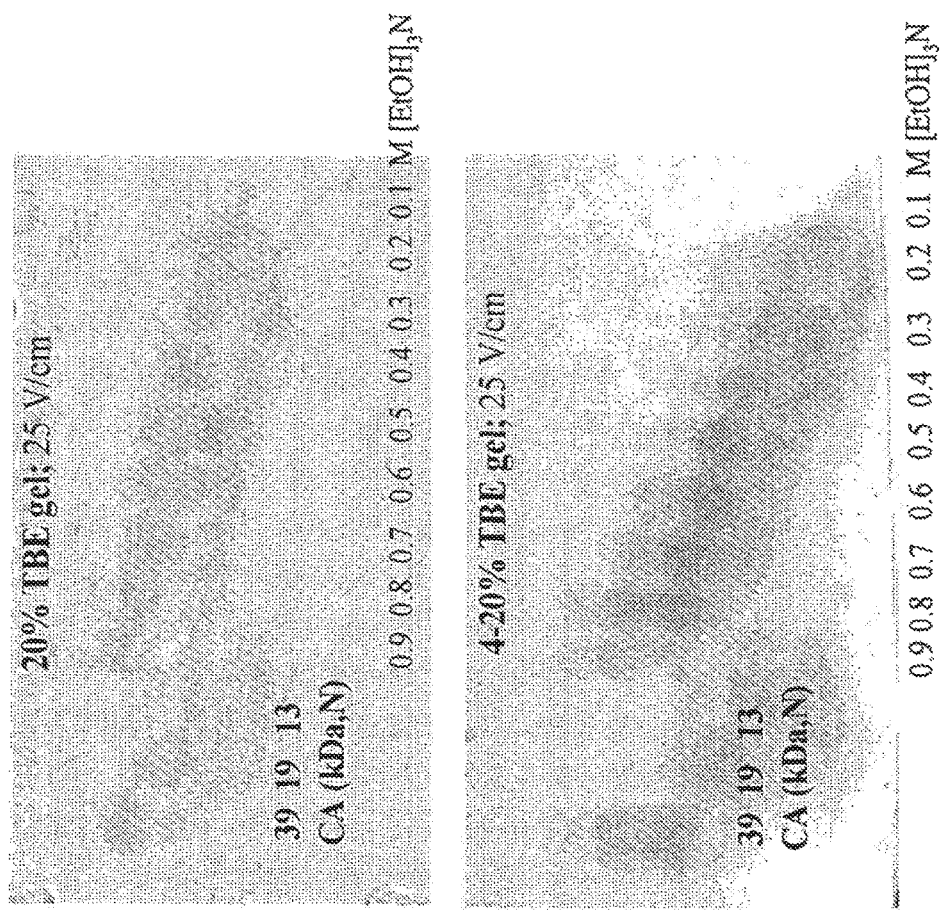
FIG. 28 shows native PAGEs of CA (22.7 kDa) IEC fractions using increasing ionic strength of triethanolamine.

The filtrates of high-pressure ultrafiltration obtained from IEC fractionation of CA (22.7 kDa, pd 1.34) were concentrated by Vivaflow (mwco 3 kDa). These CA samples were analysed with the corresponding filters of the high-pressure ultrafiltration by native-PAGE using a 4-20% TBE gel (FIG. 27) for any degradation of the polymer.

Results of Example 10.2: Results from the native PAGE (FIG. 27) of the CA samples obtained by Vivaflow purification of the filtrates show that both materials had the same molecular weight. This observation of the presence of CA in the filtrates of high-pressure ultrafiltration maybe accounted for by a process known as reptation, whereby due to the flexibility, deformability and its rod-like conformation of the CA polymer, the polymer can pass through the membrane resulting in the presence of CA in the filtrates. The gel also demonstrates that both Vivaflow and ultrafiltration can be successfully employed to process the fractions obtained by IEC fractionation of CA.

Example 11

Fractionation of CA (22.7 kDa, pd1.34) by IEC Using Increasing Ionic Strength of Triethanolamine/HCl Polydispersed CA was also fractionated by Sepharose Q FF (1 ml matrix, prepacked) using a range of triethanolamine concentrations at pH 7.4 in the absence of any salt such as NaCl. Thus, CA (40 mg; 1 ml) (22.7 kDa; pd 1.34) was loaded on to a Q FF column (1 ml matrix; prepacked; Amersham Biosciences). The bound CA was eluted by passing 1 ml of each triethanolamine buffer (50, 100, 200, 300, 400, 500, 600, 700, 800, 900, 1000, 1100 and 1200 mM triethanolamine) through the column at a flow rate of 1 ml/min with a final wash of the column using 200 mM triethanolamine. The samples were directly lyophilised and then analysed by native PAGE (TBE gel stained with alcian blue).

Results of Example 11: FIG. 8 demonstrates that fractionation of CA can be achieved in the presence of a varying concentration of triethanolamine at pH 7.4.

Example 12

Fractionation of CA (22.7 kDa, pd 1.34) by IEC Using Increasing Ionic Strength of Triethanolamine Acetate Polydispersed CA was also fractionated by Sepharose Q FF (1 ml matrix, prepacked) using a range of triethanolamine acetate concentrations at pH 7.4 in the absence of any salt such as NaCl. The triethanolamine acetate buffer was prepared using triethanolamine and adjusting the pH to 7.4 using acetic acid. Polydispersed CA (40 mg; 1 ml) (22.7 kDa; pd 1.34) was loaded on to a Q FF column (1 ml matrix; prepacked). The bound CA was eluted by passing 1 ml of each triethanolamine acetate buffer (300, 400, 500, 600, 700, 800, 900, 1000, 1100, 1200, 1300, 1400 and 1500 mM triethanolamine acetate) through the column at a flow rate of 1 ml/min with a final wash of the column using 200 mM triethanolamine acetate. A small sample of each fraction (20.mu.l) was then buffer exchanged with water using a micro membrane dialysis system, lyophilised and then analysed by native PAGE (20% TBE gel stained with alcian blue).

Figure 29:
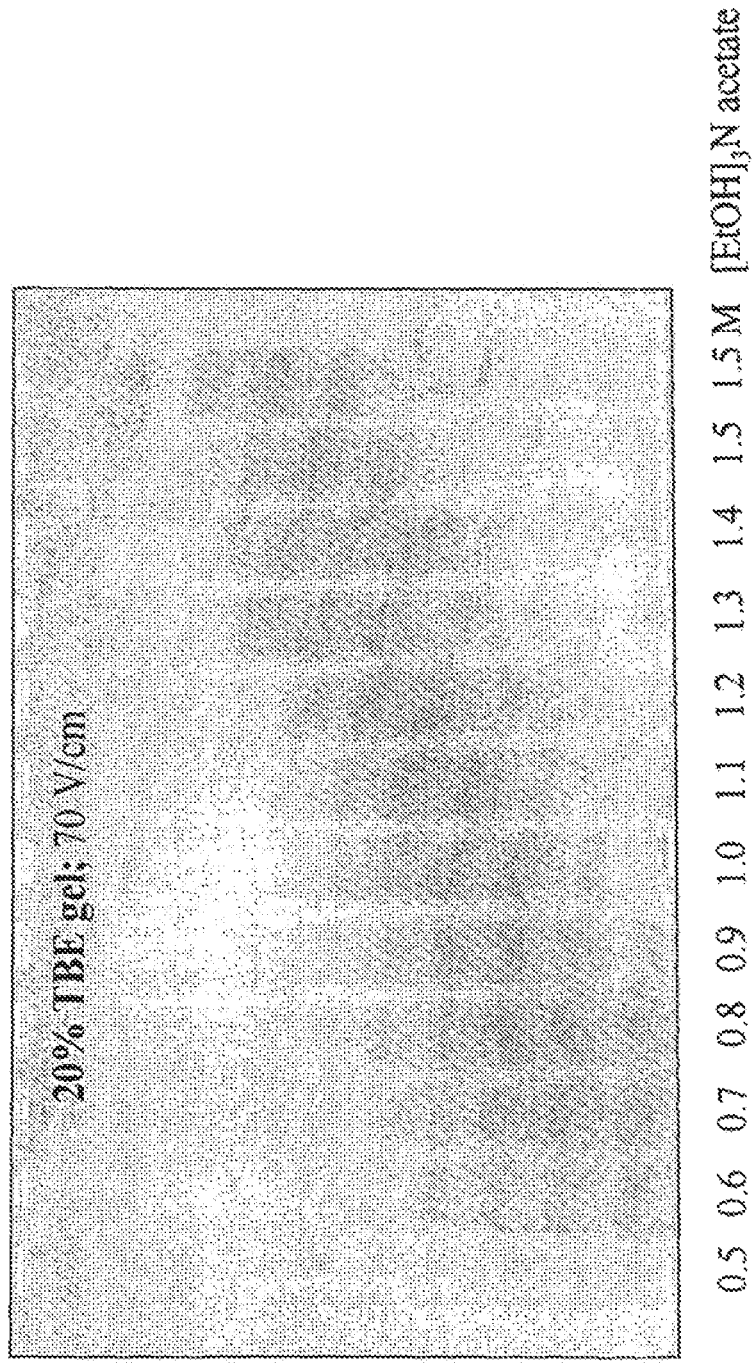
FIG. 29 shows the native PAGE of Q FF fractionation of CA (22.7 kDa) using increasing ionic strength of triethanolamine acetate.

Results of Example 12: FIG. 29 demonstrates that fractionation of CA can be successfully achieved in the presence of a varying concentration of triethanolamine at pH 7.4.

Example 13

Fractionation of CA (22.7 kDa, pd 1.34) Using a pH Gradient

HEPES and ethanolamine buffer system was used to create a pH step gradient. Buffers at pH 7.6, 7.8 and 8.0 were set up using increasing concentrations of HEPES from 10 to 50 mM and setting the pH to the appropriate value with NaOH. The concentration of sodium ions did not exceed 36 mM. Buffers at pH 8.2, 8.3, 8.5, 8.7, 8.9, 9.1, 9.3, 9.5 and 9.7 were created by mixing appropriate amounts of 1M ethanolamine (20 to 70 mM final concentration) with HEPES 50 mM (10 to 50 mM final concentration) and setting the pH with NaOH, making sure that the sodium ion concentration did not exceed 30 mM. The final buffer was a 70 mM ethanolamine pH 11.

30 mg of polydispersed CA (22.7 kDa; pd 1.34) was dissolved in pH 7.6 buffer (1 mL) and loaded onto a DEAE sepharose column (1 ml matrix, prepacked) also with the pH 7.6 buffer. The column was washed with 5 ml of the pH 7.6 buffer (flow rate 1 ml/min) followed by passing 2 ml of each buffer through the column, collecting 1 ml fractions. 500 il of each eluted fraction was lyophilised and then re-dissolved in 50 il of deionized water for analysis by native PAGE (20% TBE gel stained with alcian blue).

Figure 30:
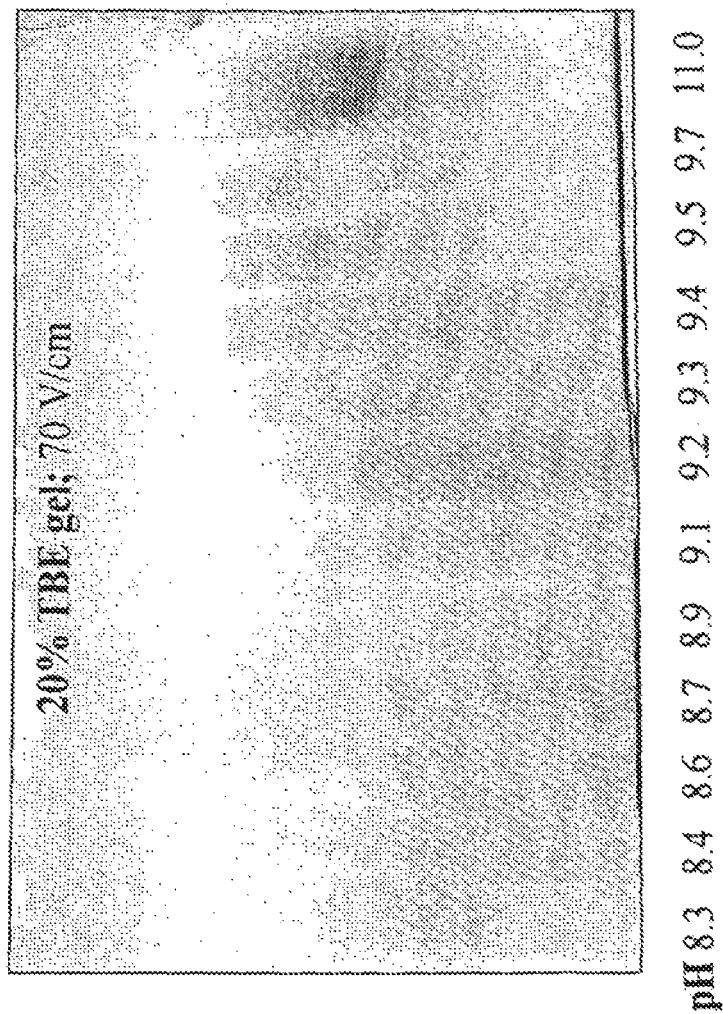
FIG. 30 shows the native PAGE of DEAE fractionation of CA (22.7 kDa) using a gradient pH system.

Results of Example 12: FIG. 30 demonstrates that fractionation of CA can be successfully achieved in the presence of an increasing pH strength. DEAE sepharose is an anion exchange matrix with a tertiary amino group, N-diethyl-amino-ethyl, which looses its charge at high pH. Thus, high pH is used to deprotonate the matrix, change its charge and elute any species bound by ionic interactions on the column. A mixed gradient can also be used where a pH gradient is first used to fractionate the low molecular weight species followed by an ionic strength gradient to elute the higher m.w. species.

REFERENCES

Bendele, A., Seely, J., Richey, C., Sennello, G., Shopp, G., Renal tubular vacuolation in animals treated with polyethylene-glycol conjugated proteins, Toxicological sciences, 42 (1998) 152-157.

Beranova, M., Wasserbauer, R., Vancurova, D., Stifter, M., Ocenaskova, J., Mora, M., Biomaterials, 11 (2000) 521-524.

Brocchini, S., Polymers in medicine: a game of chess. Drug Discovery Today, 8, (2003) 111-112.

Cheng T. Wu, M., Wu, P., Chern, J, Roffer, S R., Accelerated clearance of polyethylene glycol modified proteins by anti-polyethylene glycol IgM. Bioconjugate chemistry, 10 (1999) 520-528.

Cho, J. W. and Troy, F. A., PSA engineering: Synthesis of polysialylated neoglycosphingolipid by using the polytransferase from neuroinvasive E. coli K1, Proceedings of National Academic Sciences, USA, 91 (1994) 11427-11431.

Constantino, P. et al. (1999) Vaccine 17, 1251-63.

Conyers, C. D., Lejeune, L., Shum, K., Gilbert, C., Shorr, R. G. L, Physiological effect of polyethylene glycol conjugation on stroma-free bovine hemoglobin in the conscious dog after partial exchange transfusion, Artificial organ, 21 (1997) 369-378.

Dyer, J. R., Use of periodate oxidation in biochemical analysis, Methods of Biochemical Analysis, 3 (1956) 111-152.

Fernandes, A. I., Gregoriadis, G., Polysialylated asparaginase: preparation, activity and pharmacokinetics, Biochimica et Biophysica Acta, 1341 (1997) 26-34.

Fernandes, A. I., Gregoriadis, G., Synthesis, characterization and properties of polysialylated catalase, Biochimica et Biophysica Acta, 1293 (1996) 92-96.

Fernandes, A. I., Gregoriadis, G., The effect of polysialylation on the immunogenicity and antigenicity of asparaginase: implications in its pharmacokinetics, International Journal of Pharmaceutics, 217 (2001) 215-224.

Fleury, P., Lange, J., Sur l'oxydation des acides alcools et des sucres par l'acid periodique, Comptes Rendus Academic Sciences, 195 (1932) 1395-1397.

Gregoriadis, G., Drug and vaccine delivery systems, in: PharmaTech, World Markets Research Centre Limited, London (2001) 172-176.

Gregoriadis, G., Fernandes, A., McCormack, B., Mital, M., Zhang, X, Polysialic acids: Potential for long circulating drug, protein, liposome and other microparticle constructs, in Gregoriadis, G and McCormack, B (Eds), Targeting of Drugs, Stealth Therapeutic Systems, Plenum Press, New York (1998) 193-205.

Gregoriadis, G., Fernandes, A., Mital, M., McCormack, B., Polysialic acids: potential in improving the stability and pharmacokinetics of proteins and other therapeutics, Cellular and Molecular Life Sciences, 57 (2000) 1964-1969.

Gregoriadis, G., McCormack, B., Wang, Z., Lifely, R., Polysialic acids: potential in drug delivery, FEBS Letters, 315 (1993) 271-276.

Hreczuk-Hirst, D., Jain, S., Genkin, D., Laing, P., Gregoriadis, G., Preparation and properties of polysialylated interferon-a-2b, MPS Annual Meeting, 2002, Toronto, Canada, M1056

Hunter, A. C, Moghimi, S. M., Therapeutic synthetic polymers: a game of Russian Roulette. Drug Discovery Today, 7 (2002) 998-1001.

Jain, S., Hirst, D. H., McCormack, B., Mital, M., Epenetos, A., Laing, P., Gregoriadis, G., Polysialylated insulin: synthesis, characterization and biological activity in vivo, Biochemica et. Biophysica Acta, 1622 (2003) 42-49.

Jain, S., Hirst, D. H., Laing, P., Gregoriadis, G., Polysialylation: The natural way to improve the stability and pharmacokinetics of protein and peptide drugs, Drug Delivery Systems and Sciences, 4(2) (2004) 3-9.

Jennings, H. J., Lugowski, C., Immunogenicity of groups A, B, and C meningocochal polysaccharide tetanus toxoid conjugates, Journal of Immunology, 127 (1981) 1011-1018.

Lifely, R., Gilhert, A. S., Moreno, C. C., Sialic acid polysaccharide antigen of *Neisseria meningitidis* and *Escherichia coli*: esterification between adjacent residues, Carbohydrate Research, 94 (1981) 193-203.

Mital, M., Polysialic acids: a role for optimization of peptide and protein therapeutics, Ph.D. Thesis, University of London, 2004.

Muflenhoff, M., Ectehardt, M., Gerardy-Schohn, R., Polysialic acid: three-dimensional structure, biosynthesis and function, Current opinions in Structural Biology, 8 (1998) 558-564.

Park, J. T., Johnson, M. J., A submicrodetermination of glucose, Journal of Biological Chemistry, 181 (1949) 149-151.

Ravenscroft, [Sanjay please add bibliographic details, I don't have this reference].

Roth, J., Rutishauser, U., Troy, F. A. (Eds.), Polysialic acid: from microbes to man, Birkhauser Verlag, Basel, Advances in Life Sciences, 1993.

Rouser G, Fleischer S, Yamamoto A; Lipids, 1970, 5, 494-496.

Rutishauser, U., Polysialic acid as regulator of cell interactions in: R. U. Morgoles and R. K. Margalis (eds.), Neurobiology of Glycoconjugates, pp 367-382, Plenum Press, New York, 1989.

Satake, K., et. al., J. Biochem., 47, 654, (1960).

Shriner, R. L., Fuson, R. D. C., Curtin, D. Y., Morill, T. C., The Systematic Identification of Organic Compounds, 61 ed., Wiley, New York, 1980.

Svennerholm, L., Quantitative estimation of sialic acid II: A calorimetric resorcinol-hydrochloric acid method, Biochimca et Biophysica Acta, 24 (1957)604-611.

Troy, F. A. Polysialylation of neural cell adhesion molecules, Trends in Glycoscience and Glycotechnology, 2 (1990) 430-449.

Troy, F. A., Polysialylation: From bacteria to brain, Glycobiology, 2 (1992) 1-23.

Zhang, Y, Separation of oligo/polymer of 5-N-Acetylneuraminic Acid, 5-N-Glycolylneuraminic Acid, and 2-keto-3-deoxy-D-glycero-D-galacto-nonionic Acid by High Performance Anion-Exchange Chromatography with Pulsed Amperometric Detector, Analytical Biochemistry 250 (1997), 245-251.

The invention claimed is:

1. A polysialic acid which consists of sialic acid units, or oxidised, reduced, aminated and/or hydrazide derivative thereof and having a polydispersity of molecular weight (Mw/Mn) of less than 1.26, wherein the polysialic acid has a weight average molecular weight (Mw) of at least 5 kDa and is comprised of 10 to 50 sialic acid units.

2. The polysialic acid of claim 1, wherein the polysialic acid comprises up to 1000 sialic acid units.

3. The polysialic acid of claim 2, wherein the polysialic acid comprises 10 to 500 sialic acid units.

4. The polysialic acid of claim 1, wherein the polysialic acid is a poly(2,S linked sialic acid), a poly(2,9 linked sialic acid) or an alternating 2,S-2,9-linked polysialic acid.

5. A protein conjugate of the polysialic acid of claim 1.

* * * * *